US012779060B2

(12) United States Patent
Yang et al.

(10) Patent No.: US 12,779,060 B2
(45) Date of Patent: Nov. 3, 2026

(54) RADIOACTIVE ISOTOPE-LABELED, PHOTO-CROSSLINKABLE HYDROGEL, AND PREPARATION METHOD THEREFOR

(71) Applicant: SNVIA CO., LTD., Busan (KR)

(72) Inventors: Seung Yun Yang, Miryang-si (KR); Sodam Kim, Busan (KR); Sang-Gu Yim, Busan (KR); Sujeet Kumar, Miryang-si (KR); Ajeesh Chandrasekharan, Miryang-si (KR)

(73) Assignee: SNVIA CO., LTD., Busan (KR)

( * ) Notice: Subject to any disclaimer, the term of this patent is extended or adjusted under 35 U.S.C. 154(b) by 988 days.

(21) Appl. No.: 17/424,166

(22) PCT Filed: Dec. 19, 2019

(86) PCT No.: PCT/KR2019/018094
§ 371 (c)(1),
(2) Date: Jul. 20, 2021

(87) PCT Pub. No.: WO2020/159080
PCT Pub. Date: Aug. 6, 2020

(65) Prior Publication Data

US 2022/0118124 A1 Apr. 21, 2022

(30) Foreign Application Priority Data

Jan. 31, 2019 (KR) ........................ 10-2019-0012906

(51) Int. Cl.
*A61K 51/12* (2006.01)
*A61K 47/58* (2017.01)
*A61P 35/00* (2006.01)

(52) U.S. Cl.
CPC .......... *A61K 51/1213* (2013.01); *A61K 47/58* (2017.08); *A61P 35/00* (2018.01)

(58) Field of Classification Search
None
See application file for complete search history.

(56) References Cited

FOREIGN PATENT DOCUMENTS

| | | |
|---|---|---|
| EP | 0554898 A2 | 8/1993 |
| WO | 00/01733 A1 | 1/2000 |

OTHER PUBLICATIONS

Messager et al (Photochemical crosslinking of hyaluronic acid confined in nanoemulsions: towards nanogels with a controlled structure. J. Mater. Chem. B, 2013, 1, 3369-3379) (Year: 2013).*

Of Xu et al (Hyaluronic Acid-Based Hydrogels: from a Natural Polysaccharide to Complex Networks. Soft Matter. 2012 ; 8(12): 3280-3294). (Year: 2012).*

Huang et al (Co-delivery of doxorubicin and 1311 by thermosensitive. Journal of Controlled Release 220 (2015) 456-464). (Year: 2015).*

Chen Xia et al., "Photo-crosslinked HAMA hydrogel with cordycepin encapsulated chitosan microspheres for osteoarthritis treatment", Oncotarget, 2017, vol. 8, (No. 2), pp. 2835-2849.

Pilar de laPuente et al., "Injectable Hydrogels for Localized Chemotherapy and Radiotherapy in Brain Tumors", Journal of Pharmaceutical Sciences, vol. 107, Issue 3, Mar. 2018, pp. 922-933.

International Search Report for PCT/KR2019/018094 mailed Apr. 14, 2020 from Korean Intellectual Property Office.

L'ea Messager et al., "Photochemical crosslinking of hyaluronic acid confined in nanoemulsions: towards nanogels with a controlled structure", J. Mater. Chem. B, 2013, vol. 1, No. 27, pp. 3369-3379.

Pingsheng Huang et al., "Co-delivery of doxorubicin and 1311 by thermosensitive micellar-hydrogel for enhanced in situ synergetic chemoradiotherapy", Journal of Controlled Release, 2015, vol. 220, pp. 456-464.

C.A. Busatto et al., "Oil-in-microgel strategy for enzymatic-triggered release of hydrophobic drugs", Journal of Colloid and Interface Science, 2017, vol. 493, pp. 356-364.

Gulden Camci-Unal et al., "Surface-modified hyaluronic acid hydrogels to capture endothelial progenitor cells", Soft Matter, 2010, vol. 6, No. 20, pp. 5120-5126.

Yujie Ma et al., "Biocompatible macro-initiators controlling radical retention in microfluidic on-chip photopolymerization of water-in-oil emulsions", Chem. Commun., 2014, vol. 50, No. 1, pp. 112-114.

Spencer L. Fenn et al., "Visible light crosslinking of methacrylated hyaluronan hydrogels for injectable tissue repair", Journal of Biomedical Materials Research Part B: Applied Biomaterials, 2016, vol. 104, No. 6, pp. 229-1236.

* cited by examiner

*Primary Examiner* — Jake M Vu
(74) *Attorney, Agent, or Firm* — Revolution IP, PLLC

(57) ABSTRACT

A photocrosslinkable hydrogel may comprise a radioisotope-labeled photocrosslinkable compound or a pharmaceutically acceptable salt thereof, which may be used as a composition for radiotherapy, a composition for radiodiagnostic imaging and a composition for anticancer treatment. The hydrogel is excellent in staying in a local area requiring radiation treatment, so that it can be treated while minimizing damage to surrounding tissues. In addition, it can be used in combination with an anticancer agent and used as a pharmaceutical composition for anticancer treatment, so that cancer can be effectively treated. The hydrogel can be manufactured on site immediately and conveniently using a portable microfluidic system, thereby maximizing the radiation treatment effect.

2 Claims, 13 Drawing Sheets

[FIG. 1]
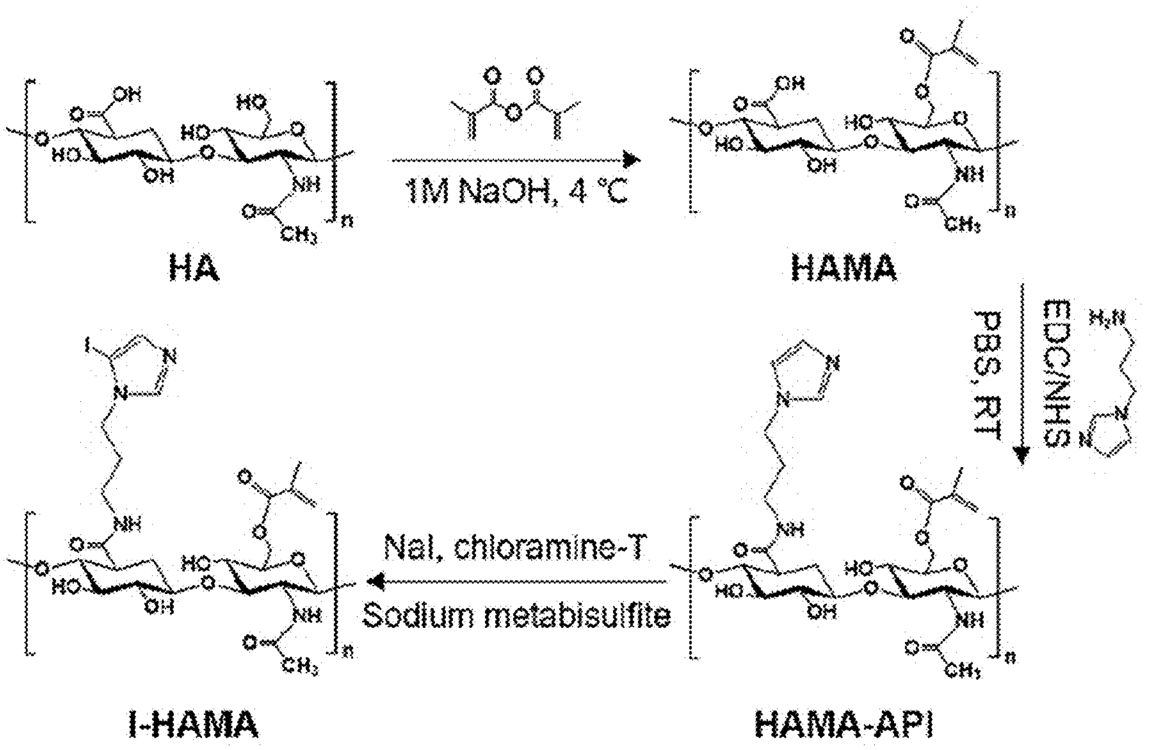

[FIG. 2]
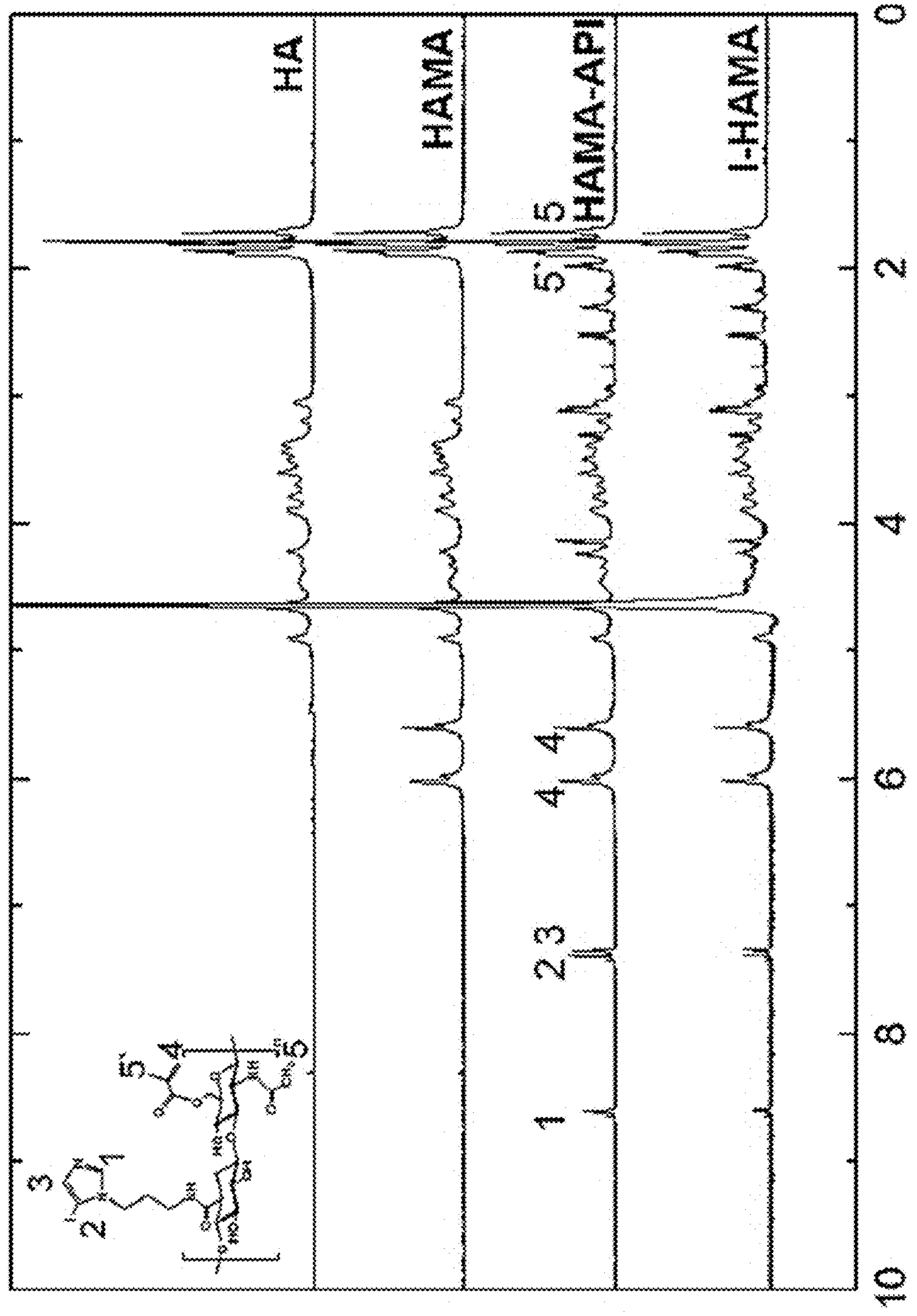

[FIG. 3]
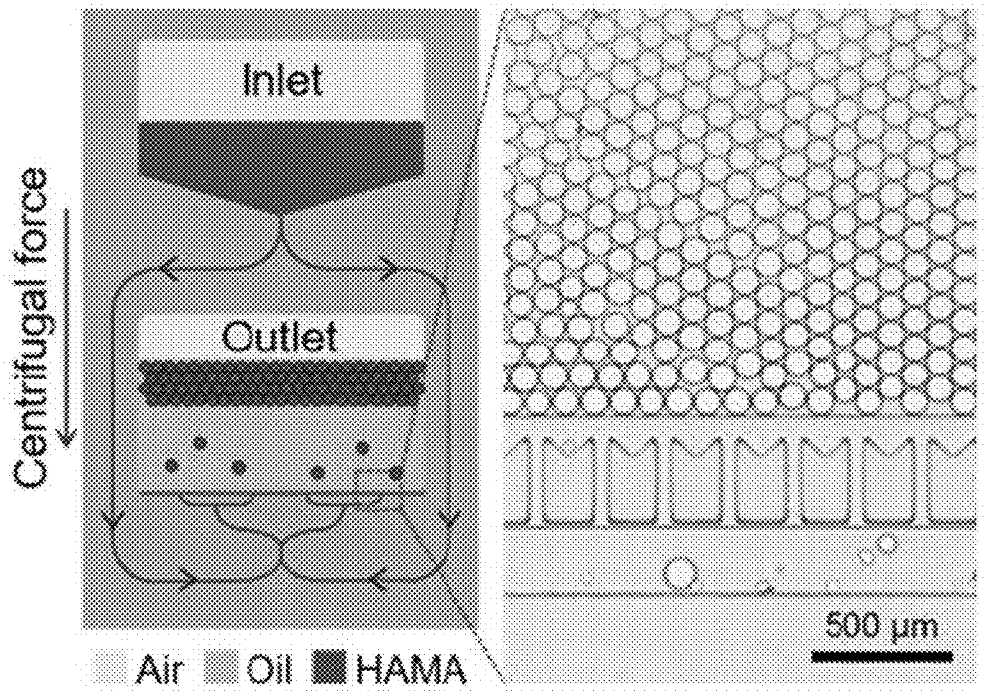
[FIG. 4]
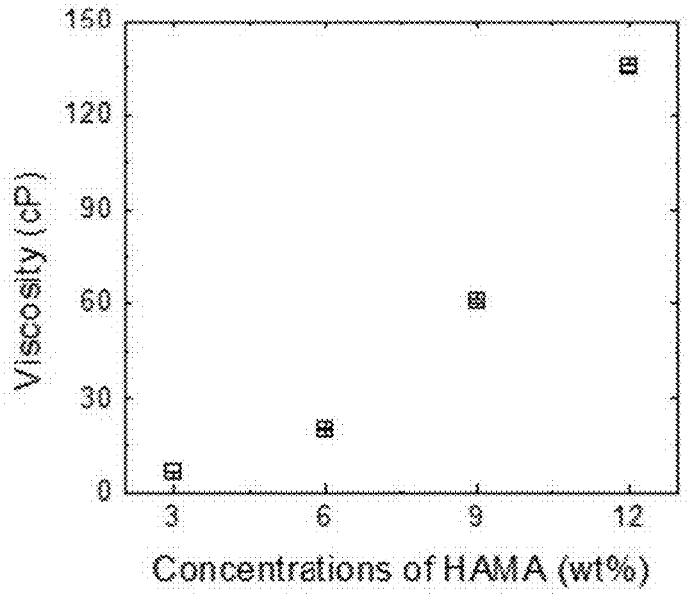

[FIG. 5]
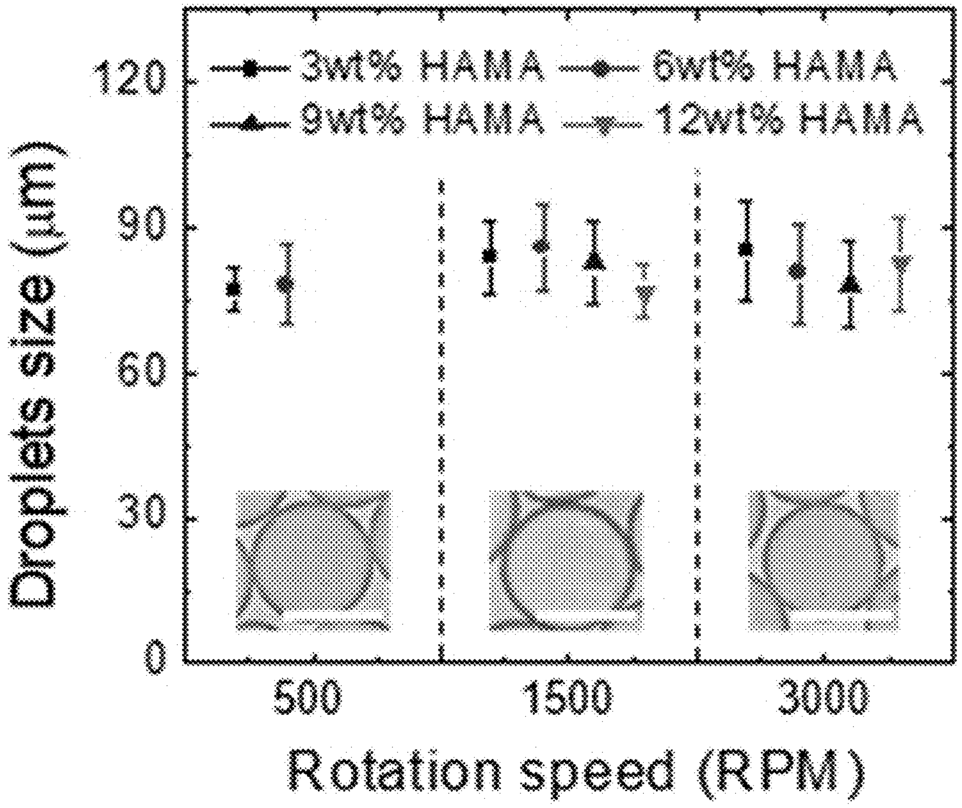
[FIG. 6]
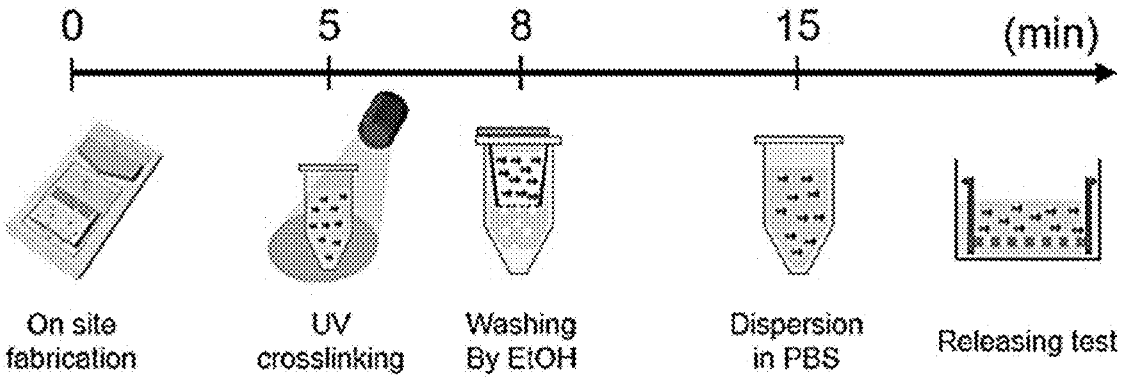

[FIG. 7]
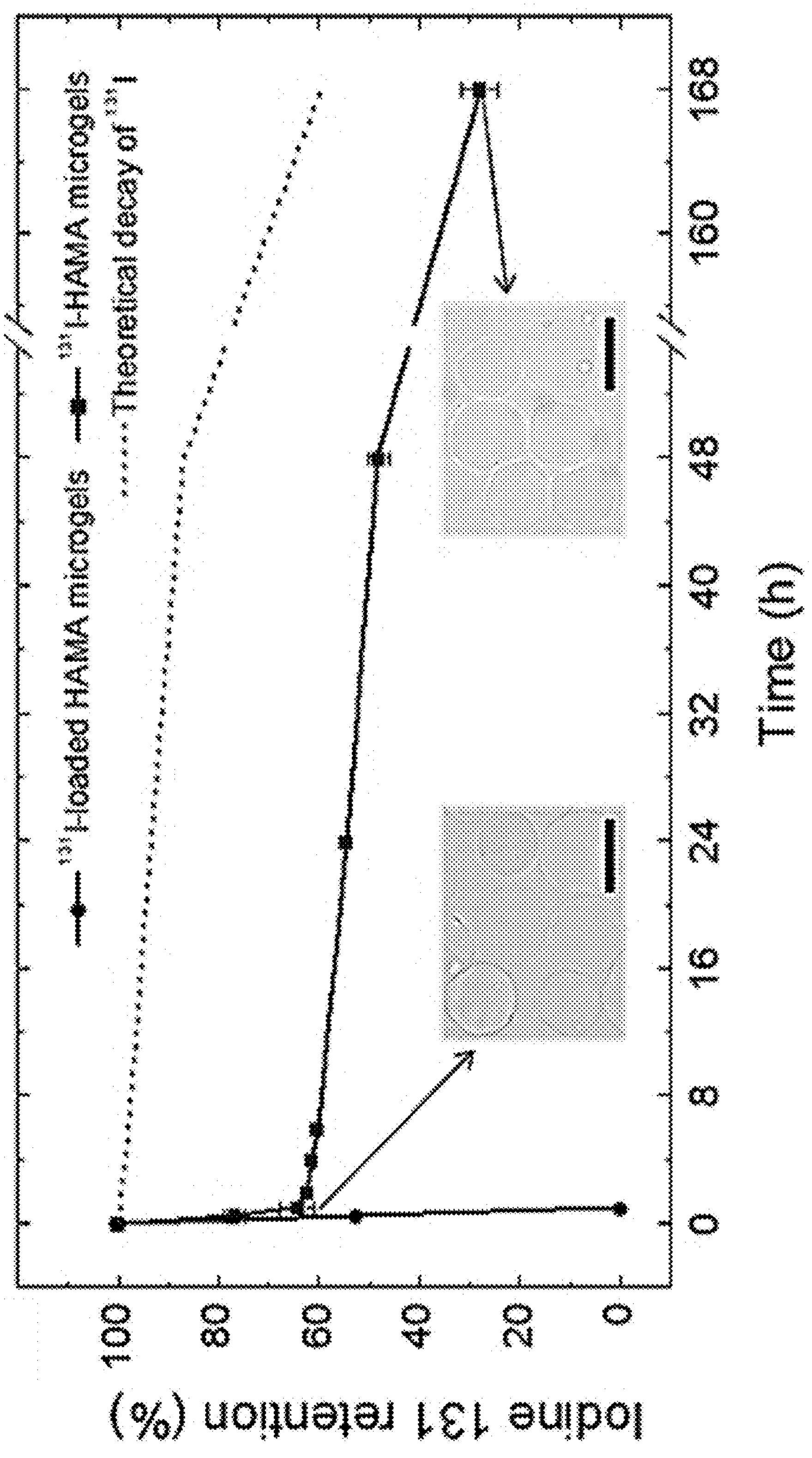

[FIG. 8]
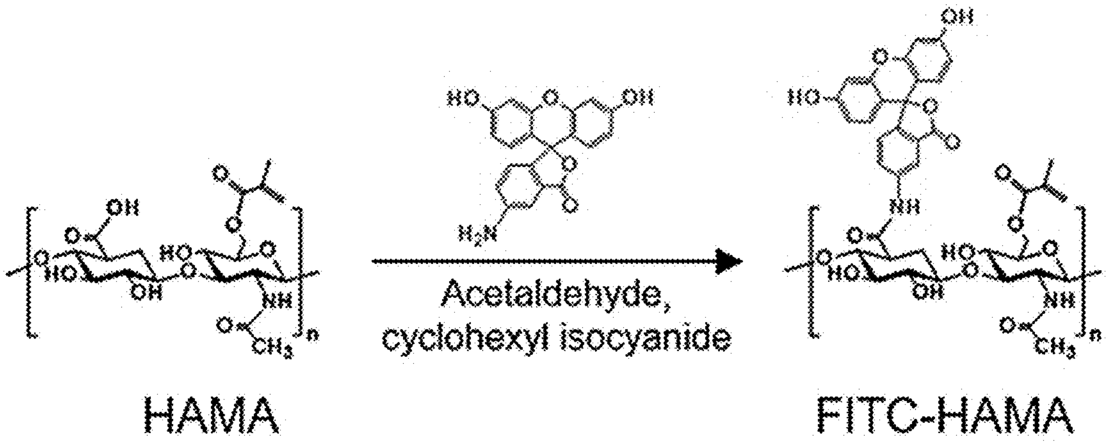
[FIG. 9]
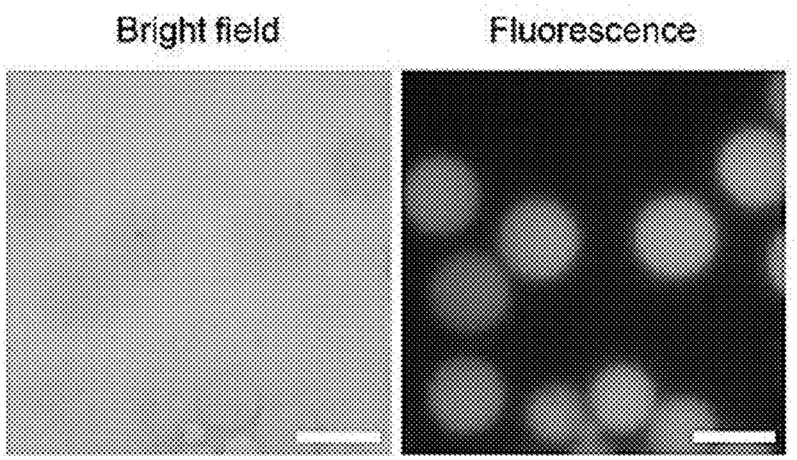
[FIG. 10]
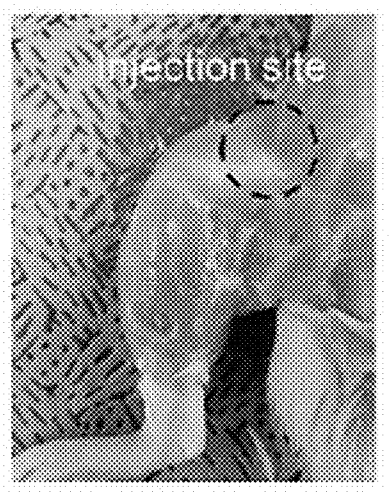

[FIG. 11]
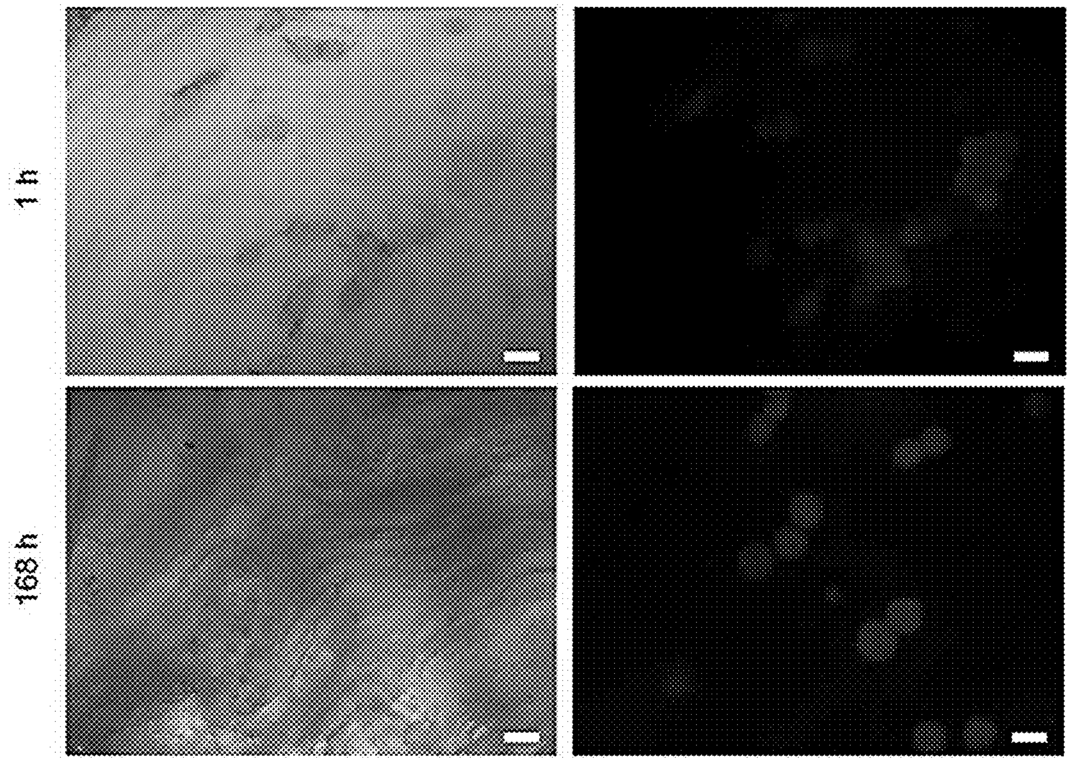
[FIG. 12]
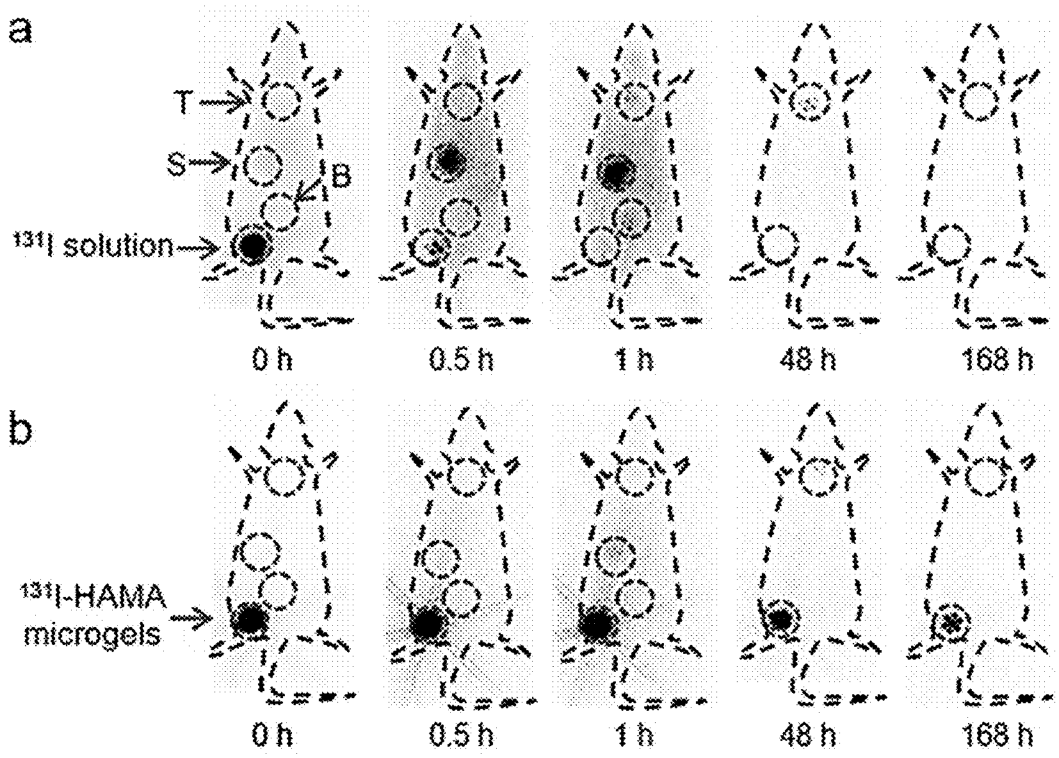

[FIG. 13]
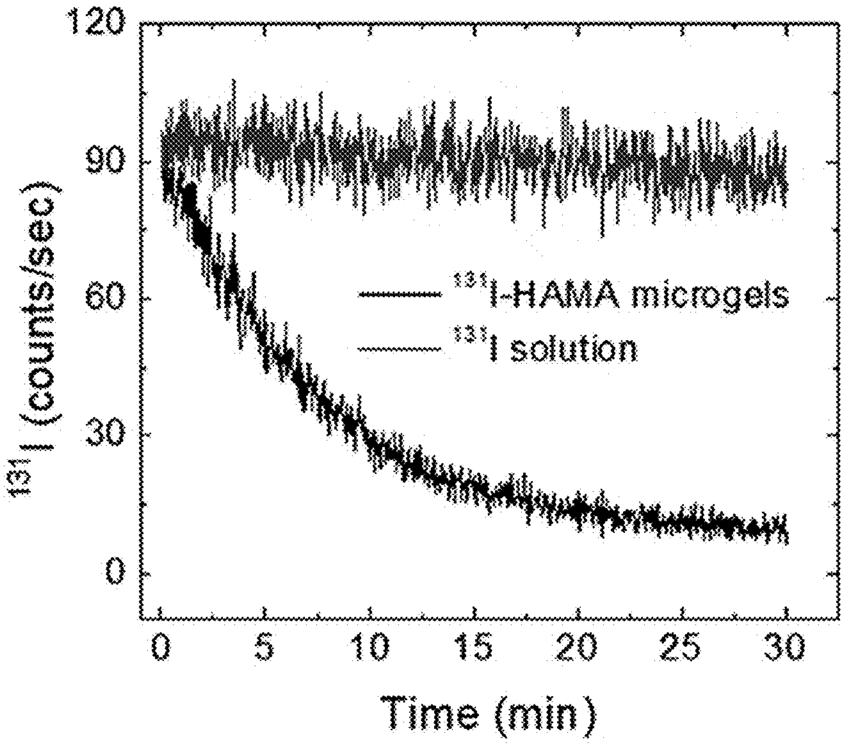
[FIG. 14]
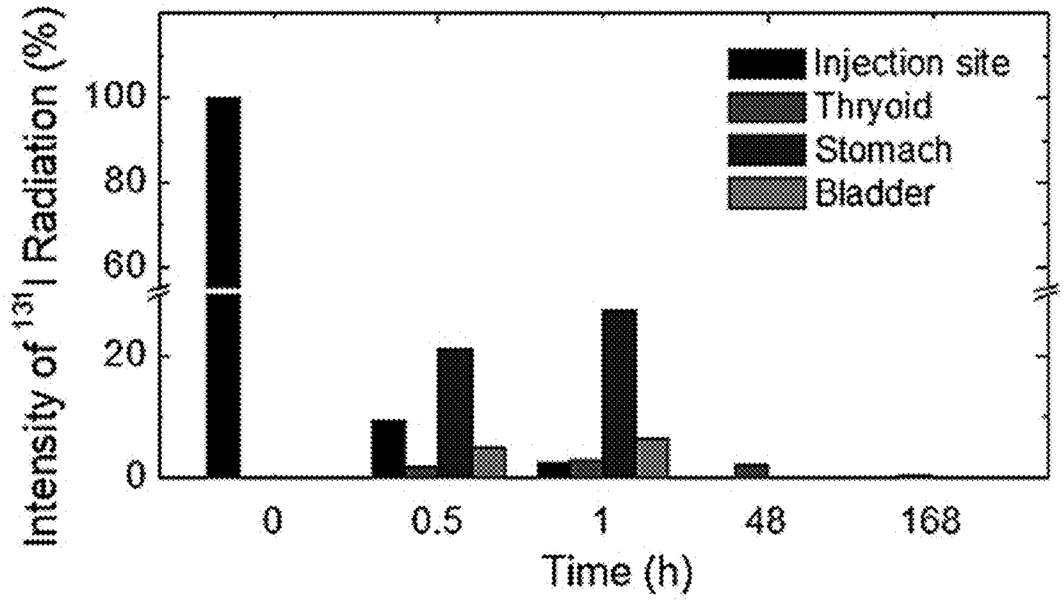

[FIG. 15]
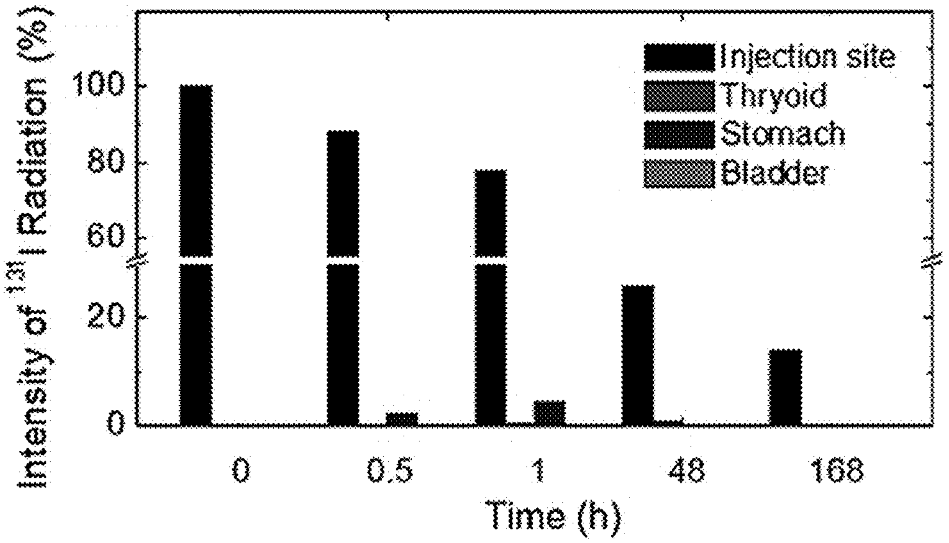
[FIG. 16]
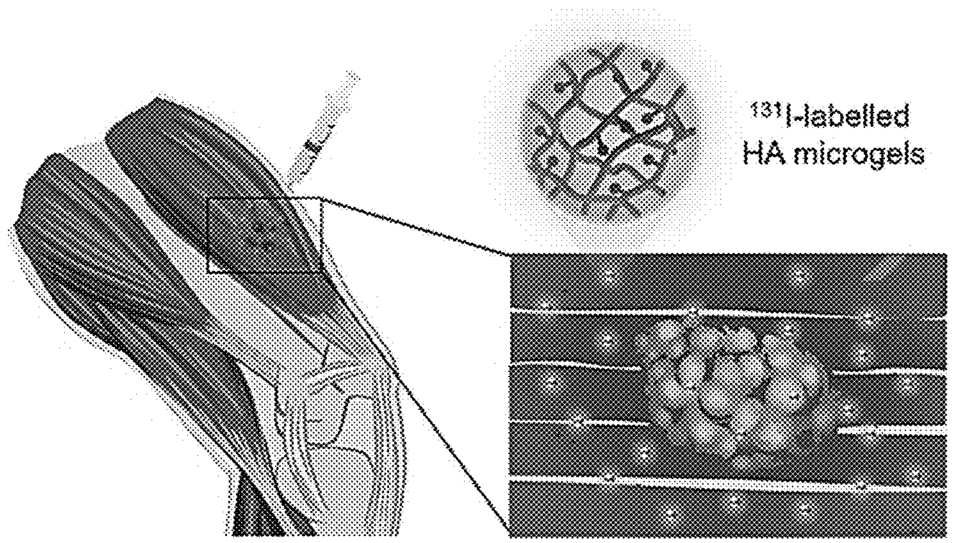
[FIG. 17]
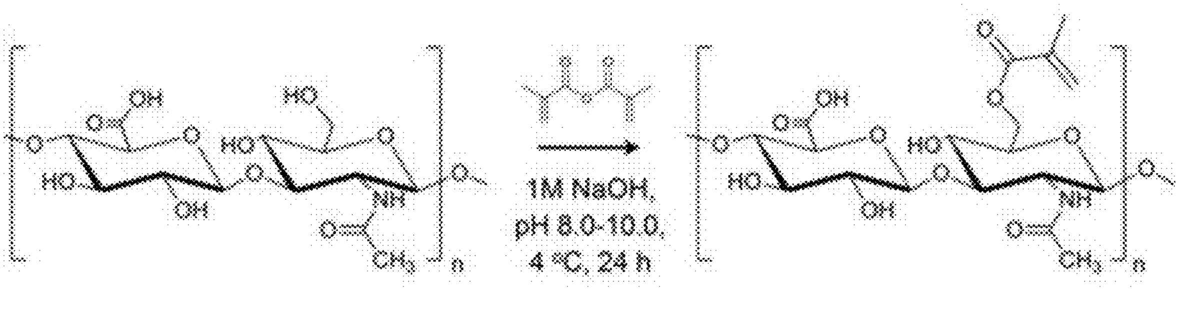

[FIG. 18]
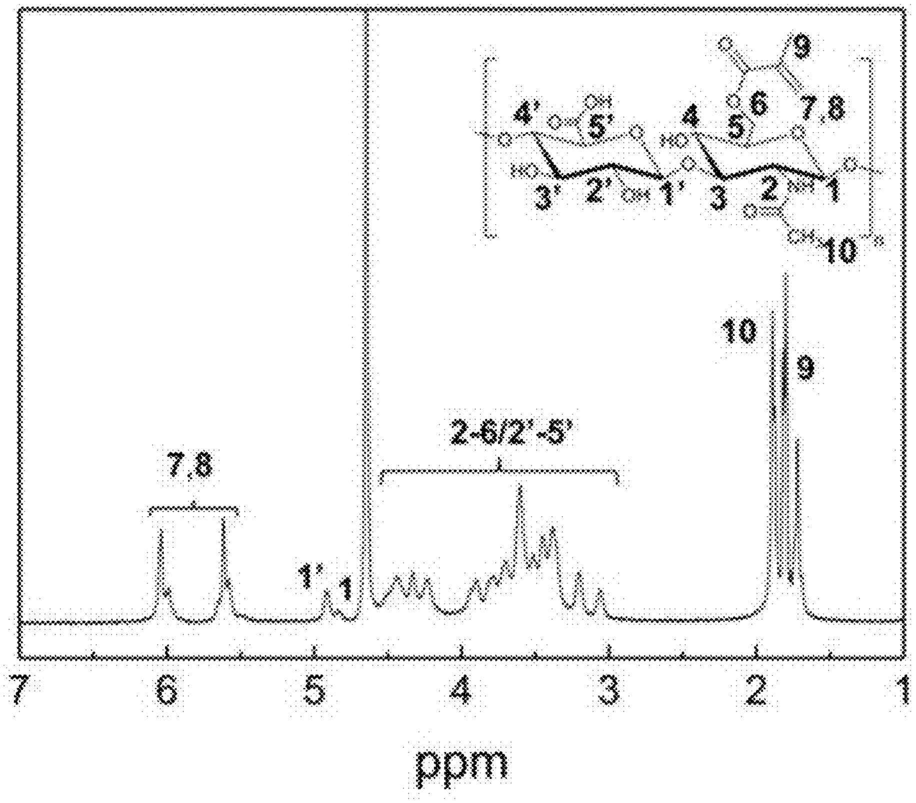

[FIG. 19]
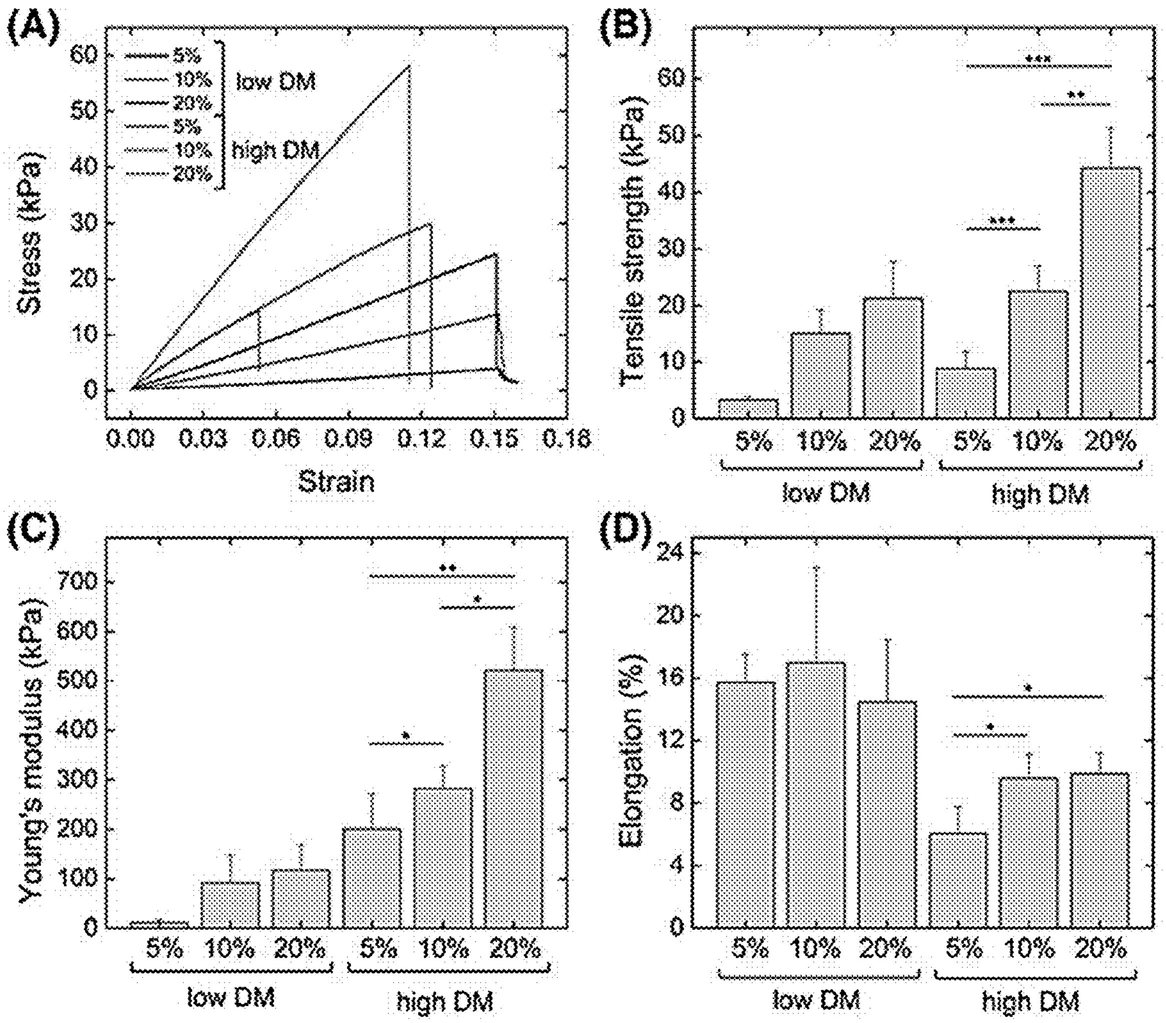

[FIG. 20]
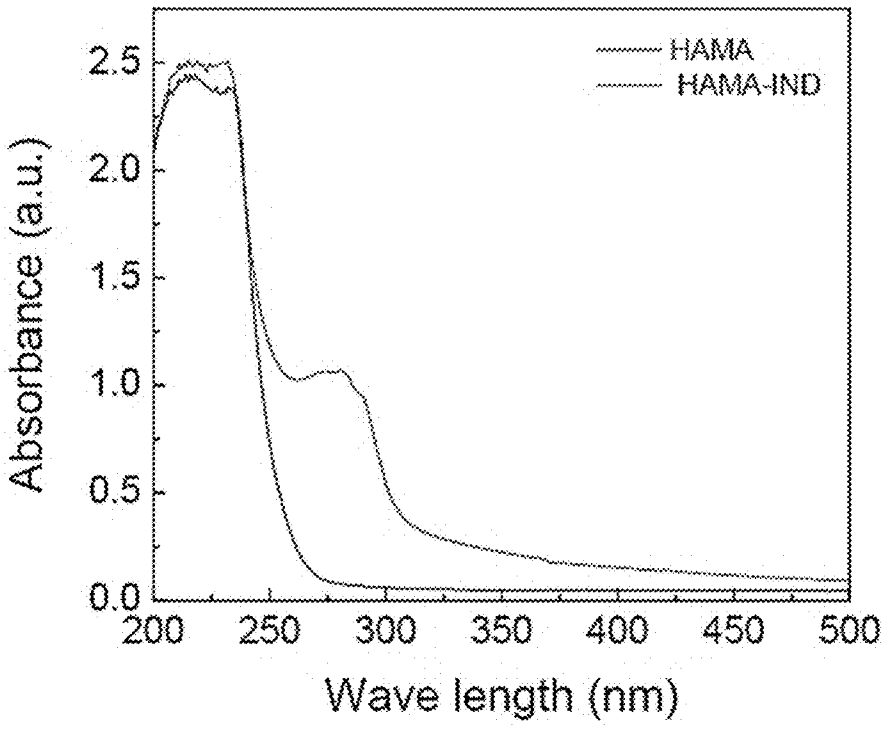

[FIG. 21]
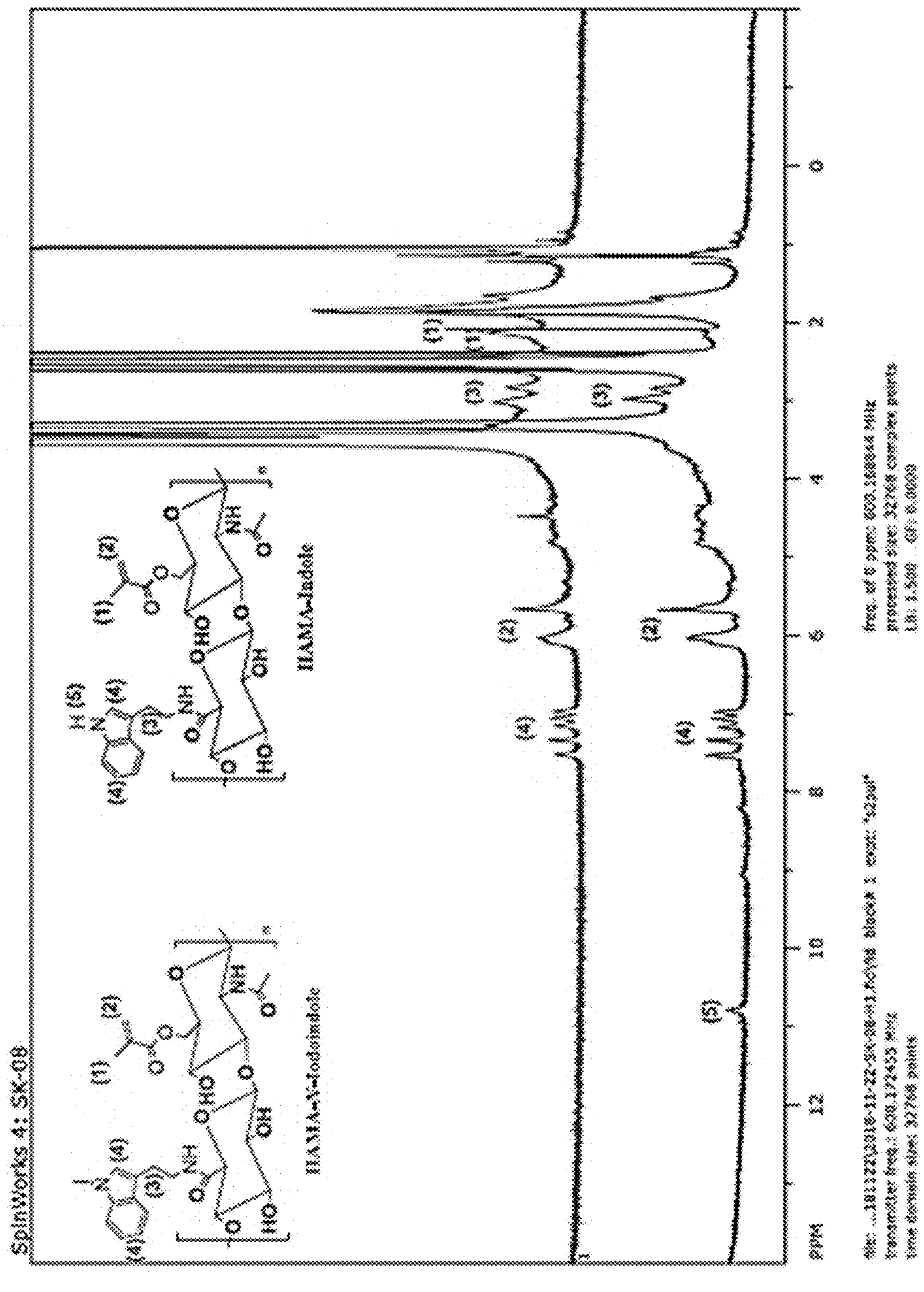

RADIOACTIVE ISOTOPE-LABELED, PHOTO-CROSSLINKABLE HYDROGEL, AND PREPARATION METHOD THEREFOR

CROSS REFERENCE TO PRIOR APPLICATIONS

This application is a National Stage Application of PCT International Patent Application No. PCT/KR2019/018094 filed on Dec. 19, 2019, under 35 U.S.C. § 371, which claims priority to Korean Patent Application No. 10-2019-0012906 filed on Jan. 31, 2019, respectively, which are all hereby incorporated by reference in their entirety.

TECHNICAL FIELD

The present invention relates to a radioactive isotope-labeled photocrosslinkable hydrogel and a method of preparing the same.

BACKGROUND ART

Cancer is one of the deadliest diseases faced by humans to date and although many advances have been made in early diagnosis and treatment, cancer still accounts for 30% of the world's deaths. Chemotherapy, one of the methods of treating cancer, is popularly used, but it is difficult to control the concentration of the drug and has a limitation of low targeting ability to the tumor site. External radiotherapy is a relatively well-controlled and regulated treatment method that induces radiation in the body through a device to destroy tumor cells, however problems such as non-specific destruction of normal tissue adjacent to the tumor, defects in the path of the ion beam, and the need for a high radiation dose to the tissue to be infiltrated remain. In contrast, internal radiotherapy is simpler than surgical and external radiotherapy and minimizes patient's pain. The destruction of tumor cells has been induced by intravenous injection of solutions containing radioactive elements such as $^{90}Y$, $^{67}Cu$, $^{188}Re$, $^{177}Lu$, $^{131}I$ and the like.

Iodine radioactive isotope is a therapeutic agent used in internal radiotherapy that accumulates in the thyroid tissue due to the radiation ionization effect and causes apoptosis and necrosis of cancer cells. However, there is a side effect of rapidly spreading throughout the body after injection into the body and damaging unwanted organs or normal tissues. To solve this problem, iodine was labeled to or supported on the polymer to increase the retention time or target the desired site. However, the use of a carrier with low biocompatibility or a long manufacturing time lowered the efficiency and the effective retention at the desired site. Nanoparticles labeled with $^{131}I$ in poly L-lactic acid (PLLA), an amphiphilic polymer, migrated to the tumor tissue, but local delivery was difficult due to radiation detection in organs other than target organs. In addition, the $^{131}I$-labeled chitosan microhydrogel containing doxorubicin therein, an anticancer drug, is locally maintained at the injection site, but the process of manufacturing the microhydrogel is complicated, making it difficult to apply it to the clinic.

DISCLOSURE

Technical Problem

In order to solve the above problems, the present invention provides a photocrosslinkable compound or a pharmaceutically acceptable salt thereof.

The present invention provides a photocrosslinkable hydrogel for radiotherapy comprising the compound or a salt thereof, and a method of preparing the same.

In addition, the present invention provides a pharmaceutical composition for radiotherapy, radiodiagnostic imaging or anticancer treatment comprising the hydrogel.

Technical Solution

A compound or a pharmaceutically acceptable salt thereof may be represented by the following Chemical Formula 1:

[Chemical Formula 1]

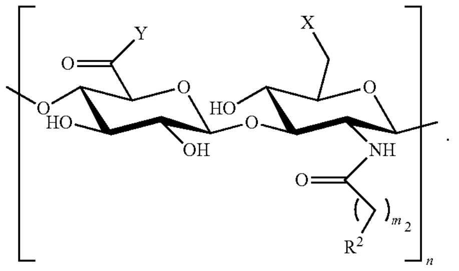

In Chemical Formula 1, X may be selected from the group consisting of photocrosslinkable acrylate, methacrylate, glycidyl methacrylate and vinyl ester, and Y may be OH or the following Chemical Formula 2:

[Chemical Formula 2]

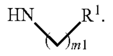

In Chemical Formulae 1 and 2, $R^1$ and $R^2$ may each be the same or different and may be selected from the group consisting of hydrogen; and imidazole, pyrrole, furan, thiophene, indole and 3,4-dihydroxyphenyl which are capable of labeling one or more radioactive isotopes, $m_1$ and $m_2$ may be integers from 0 to 2, and n may be 20 to 4,000.

The compound or a pharmaceutically acceptable salt thereof according to the present invention may be labeled with a radioactive isotope.

A photocrosslinkable hydrogel for radiotherapy according to the present invention may comprise the compound or a pharmaceutically acceptable salt thereof as an active ingredient.

A pharmaceutical composition for radiotherapy according to the present invention may comprise the hydrogel as an active ingredient.

A composition for radiodiagnostic imaging according to the present invention may comprise the hydrogel as an active ingredient.

A pharmaceutical composition for anticancer treatment according to the present invention may comprise the hydrogel and anticancer agent.

A method of preparing photocrosslinkable microhydrogel for radiotherapy may comprise preparing a photocrosslinkable compound; dissolving the prepared photocrosslinkable compound in a photoinitiator solution and then injecting it into an inlet of a microfluidic device; injecting an oil containing a surfactant into an outlet of the microfluidic device; forming microdroplets by centrifugation; and extracting the microdroplets, photocrosslinking and washing to form microgels.

Advantageous Effects

The hydrogel according to the present invention is a micro-sized hydrogel in which a photocrosslinking property is given to hyaluronic acid and radionuclides are labeled, and it is excellent in staying in a local area requiring radiation treatment, so that it can be treated while minimizing damage to surrounding tissues. Therefore, the hydrogel may be used as a pharmaceutical composition for radiotherapy or a composition for radiodiagnostic imaging. In addition, it can be used in combination with an anticancer agent and used as a pharmaceutical composition for anti-cancer treatment, so that cancer can be effectively treated.

The hydrogel according to the present invention uses hyaluronic acid which is excellent in biodegradability and biocompatibility, and has almost no immune rejection, so it can be used as a safe therapeutic composition.

The hydrogel according to the present invention can be manufactured on site immediately and conveniently using a portable microfluidic system, thereby maximizing the radiation treatment effect.

DESCRIPTION OF DRAWINGS

FIG. 1 shows a schematic view showing the synthesis process of $^{131}$I-labeled photocrosslinkable methacrylated hyaluronic acid (HAMA) according to an example of the present invention.

FIG. 2 shows a $^{1}$H NMR spectrum and a chemical structure of a hyaluronic acid-based conjugate according to an example of the present invention.

FIG. 3 shows a schematic diagram of formation of micro-droplets during fabrication of microgels according to an example of the present invention.

FIG. 4 shows a result of measuring the viscosity change according to the HAMA concentration of the microgel-forming solution according to an example of the present invention.

FIG. 5 shows the size of the HAMA microdroplet according to the revolutions per minute (RPM) of the centrifuge according to an example of the present invention.

FIG. 6 shows a preparation process on site of the $^{131}$I-HAMA microgel according to an example of the present invention.

FIG. 7 is a result of quantifying the radiation intensity in a $^{131}$I-HAMA microgel prepared according to an example of the present invention.

FIG. 8 shows a HAMA combined with a fluorescent material prepared according to an experimental example of the present invention.

FIG. 9 shows a shape of a microgel prepared according to an experimental example of the present invention.

FIG. 10 shows a site in which the FITC-HAMA microgel according to an experimental example of the present invention was injected into a rat.

FIG. 11 shows a result of the experiment according to FIG. 10.

FIG. 12 shows a SPECT image of a rat according to an experimental example of the present invention.

FIG. 13 shows the flow of $^{131}$I according to an experimental example of the present invention.

FIG. 14 shows a result of measuring the migration of the $^{131}$I solution to other tissues according to an experimental example of the present invention.

FIG. 15 shows a result of measuring the migration of a $^{131}$I-HAMA microgel solution to another tissue according to an experimental example of the present invention.

FIG. 16 shows a schematic diagram showing an application example of a microgel according to an example of the present invention.

FIG. 17 shows a preparation process of HAMA according to an example of the present invention.

FIG. 18 shows a $^{1}$H NMR spectrum of HAMA prepared according to FIG. 17.

FIG. 19 shows a graph showing the mechanical properties of a hydrogel according to an experimental example of the present invention.

FIG. 20 shows a UV/vis spectrum of HAMA and HAMA-N-indole generated according to a preparation example of the present invention.

FIG. 21 shows a $^{1}$H NMR spectrum of HAMA-N-indole and HAMA-N-iodoindole produced according to a preparation example of the present invention.

BEST MODE

Hereinafter, the present invention will be described in detail.

The present inventors produced a micro-sized hydrogel using a portable microfluidic system on site by imparting photocrosslinking properties to hyaluronic acid which is excellent in biodegradability and biocompatibility, and labeling the radionuclide $^{131}$I and injected in vivo and confirmed that it is not spread to other tissues and is locally maintained at the injected site, thereby completing the present invention.

As used herein, “radiation” refers to a phenomenon in which energy propagates through space or a material that mediates propagation, and may be emitted by various radio-nuclides.

As used herein, “radiotherapy” refers to a treatment that kills cancer cells, etc. through the action of causing chemical denaturation of nucleic acids, cell membranes, etc. essential for proliferation and survival of cells using the high energy radiation.

As used herein, “radioactivity” means the intensity of the radiation.

As used herein, “microhydrogel” refers to crosslinked particles that swell without dissolving in water at a level of several to several hundred micrometers (μm) that can be injected using a syringe, and it generally means swellable spherical or plate-shaped gel particles and may be expressed in terms such as “microgel” or “microgel”.

As used herein, “HAMA” refers to hyaluronic acid to which a methacrylate group is bonded, and may be expressed in terms such as hyaluronate methacrylate, methacrylated hyaluronic acid, etc.

As used herein, “HAMA-A” means what various kinds of cyclic compounds A are conjugated to hyaluronic acid to which a methacrylate group is bonded (HAMA).

As used herein, “HAMA-A-B” means what a radioactive isotope (B) is labeled on the cyclic compound A conjugated to the HAMA.

The present invention provides a compound represented by the following Chemical Formula 1 or a pharmaceutically acceptable salt thereof.

The compound or a pharmaceutically acceptable salt thereof may be represented by the following Chemical Formula 1:

[Chemical Formula 1]

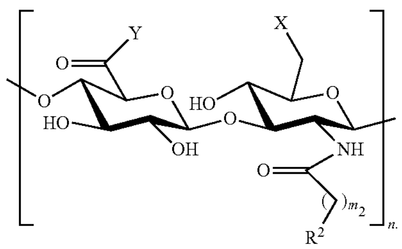

In Chemical Formula 1, X may be selected from the group consisting of photocrosslinkable acrylate, methacrylate, glycidyl methacrylate and vinyl ester, and Y may be OH or the following Chemical Formula 2:

[Chemical Formula 2]

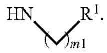

In Chemical Formulae 1 and 2, $R^1$ and $R^2$ may each be the same or different and may be selected from the group consisting of hydrogen; and imidazole, pyrrole, furan, thiophene, indole and 3,4-dihydroxyphenyl which are capable of labeling one or more radioactive isotopes, $m_1$ and $m_2$ may be integers from 0 to 2, and n may be 20 to 4,000 (number average molecular weight is 10,000 to 2,000,000), preferably 100 to 400 (number average molecular weight is 50,000 to 200,000).

More specifically, the Y may be combined with any one selected from the group consisting N-(3-aminopropyl)-imidazole (API), 3-(1H-pyrrol-1-yl)-1-propanamine, 1-(3-furyl)methanamine, thienylmethylamine, tryptamine, 3,4-dihydroxyphenylalanine (DOPA) and derivatives thereof.

Accordingly, the compound may include hyaluronate methacrylate (hereinafter, HAMA)-API, HAMA-DOPA, HAMA-pyrrol, HAMA-furan, HAMA-thiophene, HAMA-indole and derivatives thereof.

The pharmaceutically acceptable salt according to the present invention may include either a pharmaceutically acceptable basic salt or an acidic salt.

The basic salt can be used in the form of either an organic base salt or an inorganic base salt, and it may be selected from the group consisting of sodium salt, potassium salt, calcium salt, lithium salt, magnesium salt, cesium salt, aminium salt, ammonium salt, triethylaminium salt and a pyridinium salt, but it is not limited thereto.

As acidic salts, acid addition salts formed by free acids are useful. Inorganic acids and organic acids can be used as the free acid, hydrochloric acid, bromic acid, sulfuric acid, sulfurous acid, phosphoric acid, double phosphoric acid, nitric acid, etc. can be used as inorganic acids, and citric acid, acetic acid, maleic acid, malic acid, fumaric acid, glucoic acid, methanesulfonic acid, benzenesulfonic acid, camphorsulfonic acid, oxalic acid, malonic acid, glutaric acid, acetic acid, glycolic acid, succinic acid, tartaric acid, 4-toluenesulfonic acid, galacturonic acid, embonic acid, glutamic acid, citric acid, aspartic acid, stearic acid, and the like can be used as organic acids. Preferably, hydrochloric acid may be used as the inorganic acid and methanesulfonic acid may be used as the organic acid.

In addition, the compound according to the present invention may include all salts, hydrates and solvates that can be prepared by conventional methods, as well as pharmaceutically acceptable salts. For example, it can be prepared by a conventional method and the addition salt can be prepared by dissolving the compound in a water-miscible organic solvent such as acetone, methanol, ethanol or acetonitrile and adding an excessive amount of organic base or an aqueous base solution of an inorganic base, followed by precipitation or crystallization. Alternatively, it may be prepared by evaporating a solvent or an excess base and drying to obtain an addition salt, or by suction filtration of the precipitated salt.

In the compound or salt according to the present invention, the radioactive isotope may include a halogenated radioactive isotope, and may be at least one selected from the group consisting of $^{131}I$, $^{125}I$, $^{124}I$, $^{123}I$, $^{18}F$, $^{19}F$, $^{177}Lu$ and $^{211}At$, preferably, it may be $^{131}I$, but it is not limited thereto.

The present invention provides a compound or a pharmaceutically acceptable salt thereof, wherein a radioisotope is labeled on the compound represented by the Chemical Formula 1 or a pharmaceutically acceptable salt thereof.

The radioactive isotope may include a halogenated radioactive isotope, and may be at least one selected from the group consisting of $^{131}I$, $^{125}I$, $^{124}I$, $^{123}I$, $^{18}F$, $^{19}F$, $^{177}Lu$ and $^{211}At$, and preferably $^{131}I$, but it is limited thereto.

The radioactive isotopes may be labeled on at least one cyclic compound selected from the group consisting of imidazole, pyrrole, furan, thiophene, indole and 3,4-dihydroxyphenyl, which contained in the compound, and more specifically, may be labeled on a cyclic compound selected from the group consisting of N-(3-aminopropyl)-imidazole (API), 3-(1H-pyrrol-1-yl)-1-propanamine, 1-(3-furyl)methanamine, thienylmethylamine, tryptamine, OPA (3,4-dihydroxyphenylalanine) and derivatives thereof, to form HAMA-API-I, HAMA-DOPA-I, HAMA-pyrrol-I, HAMA-furan-I, HAMA-thiophene-I, HAMA-N-iodoindole and derivatives thereof. More details will be described later according to the following preparation examples.

The present invention provides a photocrosslinkable hydrogel for radiotherapy.

The photocrosslinkable hydrogel for radiotherapy according to the present invention may comprise a compound or a pharmaceutically acceptable salt thereof, which labels with a radioactive isotope, specifically at least one selected from the group consisting of $^{131}I$, $^{125}I$, $^{124}I$, $^{123}I$, $^{18}F$, $^{19}F$, $^{177}Lu$ and $^{211}At$ on the compound represented by Chemical Formula 1 or a pharmaceutically acceptable salt thereof, as an active ingredient.

The hydrogel is a highly hydrated material composed of a hydrophilic polymer that forms a three-dimensional network organized in the crosslinking process so as to form a soft and porous structure.

The hydrogel may have an average particle size of a micrometer (μm) unit, and specifically, may be a microgel having an average particle size of 10 to 200 μm, preferably 50 to 100 μm. According to an experimental example of the present invention, the microgel may be injected into a human body for radiation treatment.

The present invention provides a pharmaceutical composition for radiotherapy.

The pharmaceutical composition for radiotherapy according to the present invention may comprise a photocrosslinkable hydrogel as an active ingredient.

In the present invention, "treatment (or therapy)" may be included without limitation as long as it is any action that improves or benefits a disease or disease such as cancer.

In the pharmaceutical composition according to the present invention, the type of disease to be subjected to radiation treatment is not particularly limited, but, for example, may be one or more cancers selected from the group consisting of thyroid cancer, breast cancer, biliary tract cancer, gallbladder cancer, pancreatic cancer, colon cancer, uterine cancer, esophageal cancer, gastric cancer, brain cancer, rectal cancer, lung cancer, bladder cancer, kidney cancer, ovarian cancer, prostate cancer, uterine cancer, head and neck cancer, skin cancer, blood cancer and liver cancer, and preferably breast cancer, uterine cancer, prostate cancer or skin cancer.

The pharmaceutical composition of the present invention can be administered by parenteral administration including subcutaneous, intradermal, intravenous, intramuscular, intraarticular, intrasynovial, intrasternal, intrathecal, intralesional and intracranial injection or infusion techniques, and preferably, it can be administered as an injection formulation.

Pharmaceutical compositions for parenteral administration include sterile aqueous or non-aqueous solutions, dispersions, suspensions, or emulsions, as well as sterile powders prepared immediately before use as sterile solutions or suspensions. Examples of suitable sterile aqueous and non-aqueous carriers, diluents, solvents or vehicles include water, saline, ethanol, polyols (e.g., glycerol, propylene glycol, polyethylene glycol, etc.) and mixtures thereof, vegetable oils (e.g., olive oil), injectable organic esters (e.g., ethyloleate). For example, in the case of a dispersant and a suspending agent, a coating material such as lecithin is used to maintain an appropriate specific size and a surfactant can be used to maintain an appropriate fluidity.

In addition, parenteral compositions may contain adjuvants such as preservatives, wetting agents, emulsifying agents and dispersing agents. The sterilization of the injectable formulation can be performed, for example, by filtering through a sterile filter, or by pre-sterilizing the components of the mixture before mixing, at the time of manufacture or just before administration (as in the case of a double container syringe package).

The pharmaceutical composition according to the present invention may be injected around solid cancer alone for the treatment of diseases, or may be used to treat residual or scattered cancer after surgery. In addition, it can be used in combination with hormone therapy, drug therapy and methods using biological response modifiers.

The present invention provides a composition for radiodiagnostic imaging.

The composition for radiodiagnostic imaging according to the present invention may comprise the photocrosslinkable hydrogel as an active ingredient. The radiodiagnostic image refers to radiographic image data generated by passing through or injecting radiation into a subject for diagnosis of diseases or disorders. Through the image data, the presence or absence of a disease, the size and the location of the cancer may be identified.

In addition, the present invention provides a pharmaceutical composition for anticancer treatment.

The pharmaceutical composition for anticancer treatment according to the present invention may include the photocrosslinkable hydrogel and an anticancer agent. The anticancer agent may be one or more selected from the group consisting of taxane or a derivative thereof such as docetaxel, cabazitaxel, paclitaxel, and in addition to vinblastine, vincristine, cisplatin, actinomycin-D, 5-fluouracil, cyclophosphamide, Procarbazine, Rituximab, Imatinib, Gefitinib, Erlotinib, pharmaceutically acceptable salts and hydrates thereof, but it is not limited thereto.

It is possible to treat more effectively by using the radioactive isotope of the hydrogel in combination with the anticancer agent for anticancer treatment The present invention provides a method of preparing a photocrosslinkable microhydrogel for radiotherapy. The method of preparing photocrosslinkable microhydrogel for radiotherapy according to the present invention comprises preparing a photocrosslinkable compound such as the compound; dissolving the photocrosslinkable compound in a photoinitiator solution and then injecting it into an inlet of a microfluidic device; injecting an oil containing a surfactant into an outlet of the microfluidic device; forming microdroplets by centrifugation; and extracting the microdroplets, photocrosslinking and washing to form microgels.

In the preparation method according to the present invention, a step of preparing a photocrosslinkable compound comprises reacting a biodegradable polymer selected from the group consisting of hyaluronic acid, a salt thereof and a combination thereof with methacrylate; conjugating one or more compounds selected from the group consisting of imidazole, pyrrole, furan, thiophene, indole and 3,4-dihydroxyphenyl capable of labeling one or more radioactive isotopes in a reacted reactant; and labeling a radioactive isotope on the conjugated compound.

The hyaluronic acid (HA) is a linear polysaccharide found in the extracellular matrix of soft tissues, and is a biopolymer having excellent biocompatibility and biodegradability. The "biodegradability" refers to a property that can be degraded when exposed to a physiological solution having a pH of 6 to 8, and preferably, it refers to a property that can be degraded by body fluids or microorganisms in the living body of mammals including humans.

The salt of hyaluronic acid may include inorganic salts such as sodium hyaluronate, potassium hyaluronate, calcium hyaluronate, magnesium hyaluronate, zinc hyaluronate, cobalt hyaluronate, and organic salts such as tetrabutylammonium hyaluronate, but it is not limited thereto. In the present invention, hyaluronic acid itself or a salt thereof may be used alone, or two or more types of hyaluronic acid and a salt thereof may be used in combination.

In addition to the hyaluronic acid, the biodegradable polymer may include synthetic polymers such as poly(ethylene glycol) and poly(vinyl alcohol); polysaccharides or carbohydrates such as heparan sulfate, chondroitin sulfate, chitosan and alginate; natural proteins such as gelatin, collagen, albumin, and the like as a constituent element.

The methacrylate is a photocrosslinking agent, and reacts with the hyaluronic acid to obtain a photocrosslinkable hydrogel. The "photocrosslinking agent" refers to a compound capable of inducing a radical reaction in a reaction system by forming a radical by light irradiation, and a compound that is typically used as a photocrosslinker or a photoinitiator may be used as a photocrosslinker of the present invention, but it is more preferable to use a photocrosslinking agent or a photoinitiator that is non-toxic or poorly toxic in vivo.

The photocrosslinking technique enables crosslinking on site of the precursor solution and provides better spatial and temporal control over the crosslinking density than chemical crosslinking techniques. The photocrosslinking method using ultraviolet or visible light can produce a hydrogel having a wide range of mechanical properties and degradability.

The step of reacting the polymer and methacrylate may be performed by adding dropwise the methacrylate to the biodegradable polymer solution cooled to 0 to 10° C., preferably 3 to 7° C., for 30 minutes to 2 hours, preferably for 1 hour to 1 hour and 30 minutes, and maintained for 20 to 30 hours in the range of pH 7 to 11, preferably pH 8 to 10, and thus methacrylated hyaluronic acid (hereinafter, HAMA) can be formed. HAMA formed according to the method of the above step may have a degree of methacrylation (DM) of 100% or more, that is, a high degree of substitution of methacrylate groups, and the higher the methacrylation degree, the better the mechanical properties and strength. The HAMA with improved mechanical properties can be biodegraded slowly in a living body, so that radiation treatment can be performed for an appropriate time.

Next, in the conjugation step, a compound selected from the group consisting of imidazole, pyrrole, furan, thiophene, indole and 3,4-dihydroxyphenyl, capable of labeling one or more radioactive isotopes on the formed HAMA can be conjugated. More specifically, a cyclic compound selected from the group consisting of N-(3-aminopropyl)-imidazole (API), 3-(1H-pyrrol-1-yl)-1-propanamine, 1-(3-furyl)methanamine, thienylmethylamine, tryptamine, DOPA (3,4-dihydroxyphenylalanine) and derivatives thereof may be conjugated.

In the radioisotope labeling step, the conjugated compound may be labeled with a radioisotope, for example, at least one selected from the group consisting of $^{131}I$, $^{125}I$, $^{124}I$, $^{123}I$, $^{18}F$, $^{19}F$, $^{177}Lu$ and $^{211}At$ to form photocrosslinkable compounds.

In the preparation method according to the present invention, the photocrosslinkable compound may be contained in 1 to 20% by weight of the photoinitiator solution, and the centrifugation may be performed at 1000 to 2000 RPM, preferably 1400 to 1600 RPM. Accordingly, an appropriate amount of microhydrogel for radiation treatment can be prepared.

In the preparation method according to the present invention, the microgel may be prepared as a gel-type injection formulation, and may be injected into the body to remain at the injection site for 1 to 3 weeks. In addition, it can be used immediately by producing the microgel within 10 to 60 minutes, preferably within 10 to 30 minutes on site according to the preparation method, and can be appropriately prepared and used when radiation treatment is required.

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

Preparation Example 1

Methacrylic anhydride, sodium hydroxide, N-(3-aminopropyl)-imidazole (API), 1-ethyl-3-(3-dimethylaminopropyl)-carbodiimide (EDC), N-hydroxysuccinimide (NHS), chloramine T, sodium metabisulfite, sodium iodide, dimethyl sulfoxide (DMSO), acetaldehyde, cyclohexyl isocyanide, fluorescein-amine) was purchased from Sigma-Aldrich (St. Louis MO, USA). Polydimethylsiloxane (PDMS, Sylgard 184) was purchased from Dow Corning. Pico-Surf™ 2 wt % in Novec™ 7500 was purchased from Sphere Fluidics (Cambridge, UK). Novec 7500 oil was purchased from 3M (St Paul, MN). Hyaluronic acid (HA) having a molecular weight of 90 KDa was purchased from Bioland (SK, Korea).

<Example 1> Preparation of $^{131}I$-Labeled Methacrylated Hyaluronic Acid (HAMA)

FIG. 1 illustrates a schematic view showing the synthesis process of $^{131}I$-labeled photocrosslinkable methacrylated hyaluronic acid (HAMA) according to an example of the present invention.

Referring to FIG. 1, methacrylated hyaluronic acid (hereinafter, HAMA) was prepared through an esterification reaction of the primary hydroxy group of hyaluronic acid (HA). 240 mg of hyaluronic acid was dissolved in 50 mL of deionized water at 25° C. This solution was prepared to pH 9 using 1M NaOH at 4° C., and then 420 mg of methacrylic anhydride was added, followed by stirring for 24 hours. The finished compound was dialyzed in deionized water for 96 hours with water exchange every 8 hours. The dialyzed product was freeze-dried to obtain HAMA.

HAMA-API was prepared by conjugating an API to hyaluronic acid through the amidation reaction of the carboxy group of HAMA and the amine group of N-(3-aminopropyl)-imidazole (hereinafter API). HAMA of 240 mg was dissolved in 40 mL of PBS (phosphate buffered saline, pH 7.4) at 25° C. for 4 hours. 1-ethyl-3-(3-dimethylaminopropyl)-carbodiimide (hereinafter, EDC) of 230 mg, 1.2 mmol and N-hydroxysuccinimide (hereinafter, NHS) of 276 mg, 2.4 mmol was added and stirred for 30 minutes to activate the carboxyl group. API (150 mg, 1.2 mmol) dissolved in 10 mL of PBS was added dropwise to this compound, and the reaction was performed for 12 hours. The finished compound was dialyzed in PBS and lyophilized to obtain HAMA-API.

The chloramine T method was used to replace iodine in the imidazole ring of HAMA-API. HAMA-API of 24 mg was added to a 2 mL centrifugation tube, dissolved in 500 μl of PBS, and 100 μl of NaI ($Na^{131}I$) was added and left for 10 minutes. 10 μl (5 mg/mL) of chloramine T solution dissolved in PBS was added and vortexed for 10 minutes. To terminate the reaction, 10 μl (10 mg/mL) of a sodium bisulfite solution dissolved in PBS was added. To remove the residue, 1 mL of ethanol was added to the reactant and centrifuged at 5000 RPM for 20 minutes. After removing the supernatant, iodine-labeled HAMA was obtained.

The chemical properties of the hyaluronic acid-based conjugate were analyzed through $^{1}H$-NMR (600 MHz Agilent NMR System, Palo Alto, USA).

FIG. 2 shows a $^{1}H$ NMR spectrum and a chemical structure of a hyaluronic acid-based conjugate according to an example of the present invention. Referring to FIG. 2, the methacrylate group and the API group were clearly observed in the range of 5.5-6.5 ppm and 7.0-8.5 ppm, respectively. In addition, it was analyzed that the iodinated I-HAMA decreased the intensity of carbon 5 of the imidazole ring due to iodine substitution.

<Example 2> Preparation of Photocrosslinkable HAMA Microgel

In order to minimize the decrease in radioactivity of isotope-labeled polymers, microgels must be quickly prepared on site. To this end, a HAMA microgel was prepared as a water-in-oil (W/O) emulsion using $^{131}I$-labeled photocrosslinkable hyaluronic acid through a portable centrifugal microfluidic system.

FIG. 3 shows a schematic diagram of formation of microdroplets during microgel fabrication according to an example of the present invention.

Referring to FIG. 3, first, a controlled amount of HAMA was dissolved in 200 μl of 1 wt % irgacure 2959 (aqueous photoinitiator) solution, and then injected into an inlet of a microfluidic device. 50 μl of novec oil in which 2 weight % of pico-surf was dissolved was injected into an outlet of this device. The device filled with the solution was coupled to a portable centrifuge (Micro-12, Hanil, Korea) with the outlet facing the center, and the RPM was adjusted for 3 minutes to form microdroplets. Droplets were formed by the centrifugal force applied in the direction of the outlet and the capillary phenomenon of the nozzle inside the outlet.

After extracting the microgel formed in the outlet with a pipette, it was transferred to a microtube, and the crosslinking of HAMA was completed to form a microdroplet through UV light (350-500 nm, OhmiCure S1500, Exclitas, USA). To remove the oil from the crosslinked microgel, it was introduced in a mini cell strainer (pore size: 40 μm, Bio-Rev, Japan), and centrifugation was repeated for 3 minutes at 1000 RPM with ethanol to wash off the oil and the photocrosslinker. Subsequently, the washed HAMA microgel was dispersed in PBS.

FIG. 4 shows a result of measuring the viscosity change according to the HAMA concentration of the microgel-forming solution according to an example of the present invention. Referring to FIG. 4, as the concentration of the HAMA solution increased, the viscosity of the microgel-forming solution also increased, and the corresponding viscosity was measured from 7 cP to 135 cP.

FIG. 5 shows the size of the HAMA microdroplet according to the revolutions per minute (RPM) of the centrifuge according to an example of the present invention. Referring to FIG. 5, the size of the HAMA microdroplets according to the concentration of the HAMA solution and RPM was 70-90 μm, indicating that the size of the HAMA microdroplets was not clearly changed, and the size of the generated droplets was independent of RPM. However, when the RPM is changed at the same concentration, the difference in the amount of HAMA microdroplets generated occurs. Therefore, in order to produce the desired amount of HAMA microgels on site, it is considered suitable to apply 3 to 6% by weight of HAMA under 1500 RPM conditions.

<Example 3> Preparation of $^{131}$I-HAMA Microgel on Site

FIG. 6 shows a preparation process of a $^{131}$I-HAMA microgel according to an example of the present invention on site. Referring to FIG. 6, it takes 15 minutes to prepare $^{131}$I-HAMA microgels by dispersing $^{131}$I-labeled HAMA powder in a PBS solution according to the method of preparing microgel of the Example 2, and it has the advantage of being able to produce radioactive isotope-labeled microhydrogels on site.

<Experimental Example 1> In Vitro $^{131}$I Release Experiment

A cell strainer (pore size: 70 μl, SPL) was put in a 6 well at room temperature, and a 0.3 mCi $^{131}$I-HAMA microgel was cast on the cell strainer. PBS (pH 7.4) of 5 mL was filled with in the wells filled with $^{131}$I-HAMA microgels and the radiation intensity of the $^{131}$I-HAMA microgels remaining in the cell strainer over time was measured by a CRC015R dose calibrator (Capintec Inc., Ramsey, USA).

FIG. 7 shows a result of quantifying the radiation intensity in a $^{131}$I-HAMA microgel prepared according to an example of the present invention.

Referring to FIG. 7, it shows the intensity of $^{131}$I staying in the $^{131}$I-HAMA microgel over time, and it was observed that the intensity of radiation decreased by 35% due to the release of $^{131}$I-HAMA in the $^{131}$I-HAMA microgel, which is unlabeled for the first hour or cannot participate in the crosslinking reaction, but after that, it showed a similar decrease trend with the theoretical radioactive decay, the half-life of $^{131}$I (=8.02 days). The scale of the inserted drawing represents 20 μm.

That is, the prepared radioactive microgel having a size of about 100 μm can be easily injected into a desired site through a syringe, and quantitative radiotherapy can be achieved. In addition, since the rate of decomposition and dissolution of microgels can vary depending on the degree of crosslinking, radiation treatment can be performed fora desired period of time, thereby minimizing the dose and maximizing radiation treatment to the local area, which can be expected to minimize tissue damage.

<Experimental Example 2> In Vivo Biodegradability Experiment of Photocrosslinkable HAMA Microgel Male rats (12-13 weeks old) were purchased from SamTacho (Osan, Republic of Korea). All rats were managed at the Animal Resources Center at Pusan National University (Busan, Korea).

In order to evaluate the stability of HAMA microgels in vivo, HAMA bound with a fluorescent substance was prepared. 200 mg of HAMA was dissolved in 160 mL of DI water and 70 mL of dimethyl sulfoxide (DMSO) at 25° C. 100 μl of fluorescein-amine, acetaldehyde and cyclohexyl isocyanide were added to the mixture, and the amidation reaction was performed for 24 hours.

FIG. 8 shows a HAMA combined with a fluorescent material prepared according to an experimental example of the present invention.

Referring to FIG. 8, the carboxyl group of HAMA was conjugated through an amidation reaction with fluorescein-amine. The final mixture was dialyzed in 100 mM NaCl solution for 48 hours, freeze-dried, and then fluorescein isothiocyanate (hereinafter, FITC)-conjugated HAMA microgels were prepared through a microfluidic system.

FIG. 9 illustrates a shape of a microgel manufactured according to an experimental example of the present invention.

Referring to FIG. 9, it was possible to confirm the shape of the stably conjugated FITC-HAMA microgel through a fluorescence microscope.

FIG. 10 shows a site in which the FITC-HAMA microgel according to an experimental example of the present invention was injected into a rat. Referring to FIG. 10, 0.2 mL of a solution dispersed in PBS (pH 7.4) was injected into the femoral muscles of rats with active movement in order to evaluate the biodistribution of FITC-HAMA.

FIG. 11 shows a result of the experiment according to FIG. 10.

Referring to FIG. 11, 1,168 hours after the injection of the FITC-HAMA microgel, the femoral muscle of the rat was excised, and the tissue cut to a thickness of 0.1 cm was analyzed through a fluorescence microscope (Eclipse TS100, Nikon, Japan). The FITC-HAMA microgel was stably injected into the rat femur muscle and was observed in the form of being embedded in the muscle tissue at the injection site, and no inflammation in the tissue due to polymer degradation or retention was observed.

<Experimental Example 3> In Vivo Local Retention Experiment of $^{131}$I-HAMA Microgel An experiment was performed to confirm the distribution of $^{131}$I and how long the $^{131}$I-HAMA microgel was maintained at the site injected into the body. After injecting 0.2 mL of a solution of Na$^{131}$I and $^{131}$I-HAMA microgel (1 mCi/mL) dispersed in PBS into the femoral muscle of the rat, gamma images were obtained over time with the SPECT imaging system (Infinia Hawkeye 4, GE Healthcare, USA). Within 30 minutes immediately after injection, the radioactivity at the injection site was measured with a counter per second in a dynamic mode. After 30 minutes, an image of the whole rat injected with $^{131}$I over time was obtained in static mode, and gamma counters of major tissues such as the injection site, thyroid gland and stomach were measured.

FIG. 12 shows a SPECT image of a rat according to an experimental example of the present invention.

Referring to FIG. 12, a is an injection of Na$^{131}$I solution, b is an injection of $^{131}$I-HAMA microgel solution, and a rat was injected with $^{131}$I solution having a 200 μCi radioactivity into the muscle and it was flowed to the whole body in 30 minutes, and rats injected with $^{131}$I-HAMA microgel solution could be confirmed to stay locally at the injection site even after 168 h (T: thyroid gland, S: stomach, B: bladder).

FIG. 13 shows the flow of $^{131}$I according to an experimental example of the present invention.

Referring to FIG. 13, as a result of analyzing the flow of $^{131}$I at the injection site through dynamic imaging, it was found that the spreading rate of the $^{131}$I solution in the body was faster than that of the $^{131}$I-HAMA microgel.

FIG. 14 shows a result of measuring the movement of a $^{131}$I solution to other tissues according to an experimental example of the present invention, and FIG. 15 shows a result of measuring the movement of a $^{131}$I-HAMA microgel solution to other tissues according to an experimental example of the present invention. Referring to FIG. 14 and FIG. 15, $^{131}$I solution was measured in the thyroid gland, stomach, and bladder in addition to the injection site, but $^{131}$I-HAMA microgel solution was hardly found in other sites. In addition, the radiation intensity decreased rapidly in the $^{131}$I solution, but gradually decreased with the decomposition of the hydrogel in the $^{131}$I-HAMA microgel solution.

FIG. 16 shows a schematic diagram showing an application example of a microgel according to an example of the present invention. Referring to FIG. 16, a radioactive microgel prepared with $^{131}$I-labeled photocrosslinkable hyaluronic acid (HA) may be limited to the injection site, and the residence time of the radionuclide to the target site after the injection increases due to the attachment to the muscle tissue, but the rapid absorption of body fluids can be minimized. The application of these technologies can improve radiotherapy which periodically injects patients with existing radionuclides, while also retaining the potential as a delivery agent for new injectable radionuclide preparations with low toxicity.

<Example 4> Preparation of Hyaluronic Acid with Improved Methacrylate Substitution About 1.0 g of hyaluronic acid (HA, Mw: 90 kDa; SNvia, Korea) was dissolved in 12 mL distilled water, and the pH was adjusted to 8 using 1N sodium hydroxide. After cooling the hyaluronic acid solution to 5° C., 1 or 4 times the equivalent of methacrylic anhydride (MA) was added dropwise over 1 hour to the disaccharide unit of hyaluronic acid. At the same time, 1N sodium hydroxide was added to keep the pH between 8.0 and 10.0. After maintaining the temperature and pH for an additional 23 hours, the macromer solution was dialyzed with distilled water for 3 days (Cellu Sep, nominal molecular weight cutoff 3500 Da), frozen at −55° C., freeze-dried, and stored at 20° C. and then used. $^{1}$H NMR spectrum was obtained using a Bruker 600-NMR spectrometer. This confirms the binding of the methacrylate group to hyaluronic acid which is used to calculate the degree of methacrylation (hereinafter, DM) (n=3).

FIG. 17 shows a preparation process of HAMA according to an example of the present invention.

The photocrosslinkable methacrylate groups are generally incorporated into the hyaluronic acid polymer backbone by reacting it with methacrylic anhydride under aqueous basic conditions. The primary hydroxyl group of hyaluronic acid is considered the most reactive site for transesterification. Hyaluronic acid has 4 hydroxyl groups per disaccharide unit, and all of the 4 hydroxyl groups could be incorporated with methacrylate groups.

HAMAs with different DMs can be synthesized by varying the molecular weight of hyaluronic acid, the molar ratio of methacrylic anhydride to hyaluronic acid and the reaction time. There are also other parameters that determine DM, such as pH and temperature of the reaction mixture. Methacrylic anhydride undergoes hydrolyzed in an aqueous medium, especially above pH 10.0, catalyzed by hydroxide ions to form methacrylic acid, which does not react with hyaluronic acid. Hydrolysis of methacrylic anhydride to methacrylic acid at low temperatures is considered slower. However, at this temperature, methacrylic anhydride exists in a separate phase.

Referring to FIG. 17, considering of biological activity and better solution processability, 90 kDa hyaluronic acid was selected. To synthesize HAMA with different DMs, 1-fold and 4-fold equivalents of methacrylic anhydride with respect to the disaccharide unit were reacted with hyaluronic acid. In addition, to minimize the excess hydrolysis of methacrylic anhydride and to reduce the phase separation during the reaction, it was added dropwise over 1 hour with vigorous stirring. At the same time, the pH was maintained between 8.0 and 10.0 for 24 hours at 5° C.

FIG. 18 shows a $^{1}$H NMR spectrum of HAMA prepared according to FIG. 17. $^{1}$H NMR experiments were used to determine the incorporating of methacrylate group into hyaluronic acid and the DM.

Referring to FIG. 18, $^{1}$H NMR spectrum revealed new peaks around δ 5.6 and 6.0 ppm corresponding to acrylate protons, suggesting incorporation of methacrylate group into hyaluronic acid. The DM was calculated from the relative integration of the methacrylate protons (5.6 and 6.0 ppm) to the methyl protons in hyaluronic acid (1.9 ppm), and this gave a value of 46±4% and 181±36% per disaccharide unit for 1- and 4-equivalents of methacrylic anhydride, respectively.

The molecular weight of hyaluronic acid and its derivatives were estimated with a gel permeation chromatography system. They showed similar polymer molecular weight distribution, indicating no premature crosslinking or significant chain cleavage during the reaction. Above 100% methacrylation suggests that at least one hydroxyl group was substituted when 4-equivalents of methacrylic anhydride were used.

That is, excessive hydrolysis of methacrylic anhydride was minimized by the slow addition of methacrylic anhydride over a period of 1 hour with vigorous stirring and maintaining the pH between pH 8.0 and 10.0 at 5° C. for 24 hours according to the Example 4, resulting in a high DM (>100%) can be obtained with a 4-fold excess of methacrylic anhydride.

<Experimental Example 4> Mechanical Properties of HAMA Hydrogel with Improved Methacrylate Substitution Briefly, polymer precursor solutions at different concentrations of 5% (w/v), 10% (w/v) and 20% (w/v) were photocrosslinked to prepare a tensile test structure of a width of 5 mm, a length of 20 mm and a thickness of 1.5 mm.

The hydrogels were directly analyzed on a mechanical tester (AND 210, Korea). The strain rate was set to 1 mm $min^{-1}$ for tensile testing. The ultimate tensile strengths of the samples were determined at the point of failure (fracture under tensile) of the hydrogel. The tensile strength was determined at the maximum point of the stress in the stress-strain curve.

The Young's modulus (tensile modulus) was calculated by obtaining the initial 5% of the slope in strain-stress curve. The elasticity was determined at the maximum point of the strain in the stress-strain curve.

FIG. 19 illustrates a graph showing the mechanical properties of a hydrogel according to an experimental example of the present invention. Referring to FIG. 19, (A) is the stress-strain curve of the HAMA hydrogel generated from various concentrations (5%, 10%, 20%[w/v]) of the HAMA solution (n=5) in low and high DM; (B) is a graph of tensile strength of the hydrogel; (C) is a graph of Young's modulus of the hydrogel; and (D) is a graph of elongation of the hydrogel (Asterisks mark statistical significance level of p<0.05 (*), p<0.01 () and p<0.001 (*)).

The stress-strain curve of (A) showed that the higher the concentration of the HAMA solution with high DM, the larger the slope of the curve.

As the concentration of the HAMA solution increases from 5% to 20%, the tensile strength of (B) constantly increases from 3.31±0.61 to 21.22±6.48 kPa for the low DM, and from 8.83±2.99 to 44.24±7.09 kPa for the high DM.

The Young's modulus of (C) was also found to increase with higher DM and concentration.

The elongation of (D) was varied in the range of 6 to 17% depending on DM and concentration.

<Preparation Example 1> HAMA-DOPA-1

[Reaction Scheme 1]

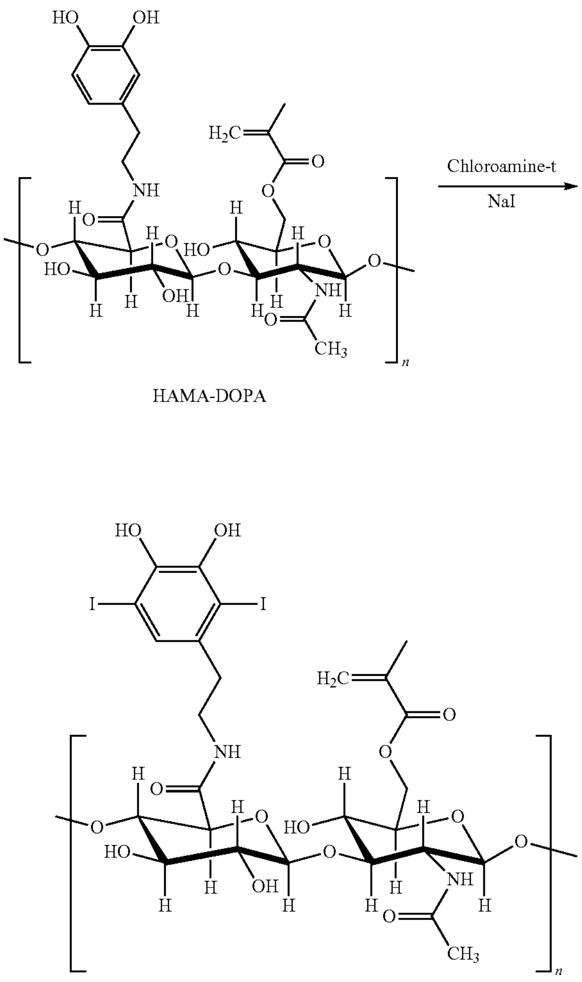

HAMA-DOPA

HAMA-DOPA-I

Reaction Scheme 1 shows the preparation process of HAMA-DOPA-I. After preparing HAMA with improved methacrylate substitution according to the Example 4, 100 mg of HAMA was dissolved in 10 mL PBS (pH 7.4) solution. After adjusting the pH to 5.5 using 1N HCl, 85.5 mg of EDC and 102.7 mg of NHS were added to the solution in the same manner as in the method of preparing HAMA-API of the Example 1, followed by stirring for 30 minutes. Thereafter, instead of the API, 126.9 mg of dopamine hydrochloride was added according to Reaction Scheme 1, and the pH of the reaction mixture was adjusted to 7 using 1N NaOH, followed by stirring at 25° C. for 24 hours. The reaction mixture was dialyzed in a pH 5.0 solution for 2 days (Cellu Sep, nominal molecular weight cutoff 3500 Da) and then dialyzed with distilled water for 1 day. The resulting solution was freeze-dried to obtain a product, and the resulting HAMA-DOPA solution was prepared, followed by labeling $^{131}I$. Since more $^{131}I$ substitutions could be made than the HAMA-API according to the Example 1, it was expected that the radiation treatment effect would also be higher.

<Preparation Example 2> HAMA-Pyrrol-I

[Reaction Scheme 2]

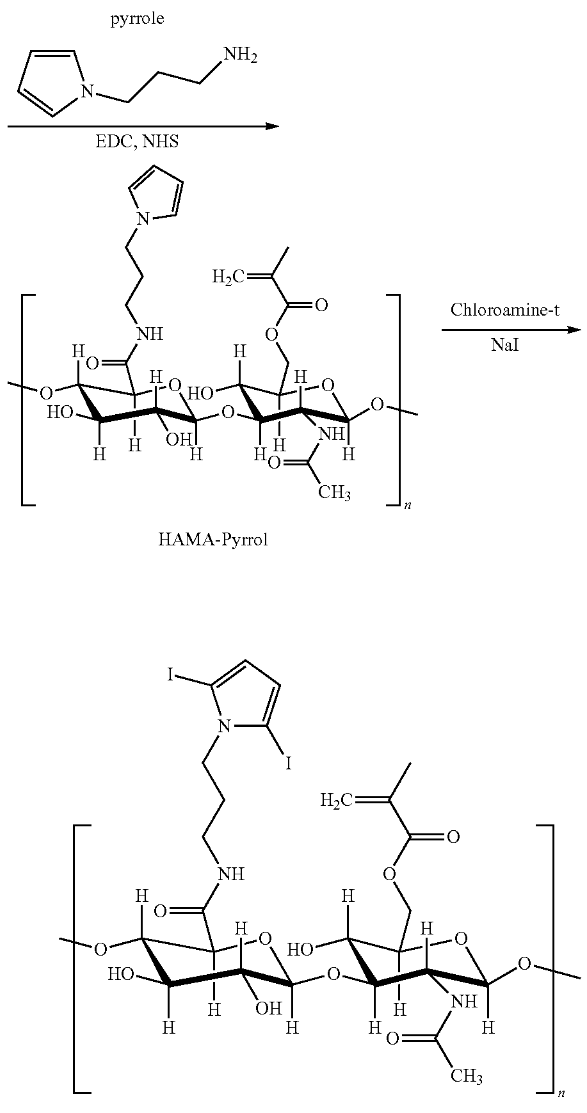

Reaction Scheme 2 shows the preparation process of HAMA-pyrrol-I. After preparing HAMA with improved methacrylate substitution according to the Example 4, 100 mg of HAMA was dissolved in 10 mL PBS (pH 7.4) solution. After adjusting the pH to 5.5 using 1N HCl, 85.5 mg of EDC and 102.7 mg of NHS were added to the solution in the same manner as in the method of preparing HAMA-API of the Example 1, followed by stirring for 30 minutes. Then, instead of the API, 110.7 mg of 3-(1H-pyrrol-1-yl)-1-propanamine was added according to the Reaction Scheme 2 and stirred at 25° C. for 24 hours. The reaction mixture was dialyzed for 2 days in a pH 5.0 solution, and then dialyzed for 1 day with distilled water. The resulting solution was freeze-dried to obtain a product, and the resulting HAMA-pyrrol solution was prepared, followed by labeling $^{131}I$.

<Preparation Example 3> HAMA-Furan-I

[Reaction Scheme 3]

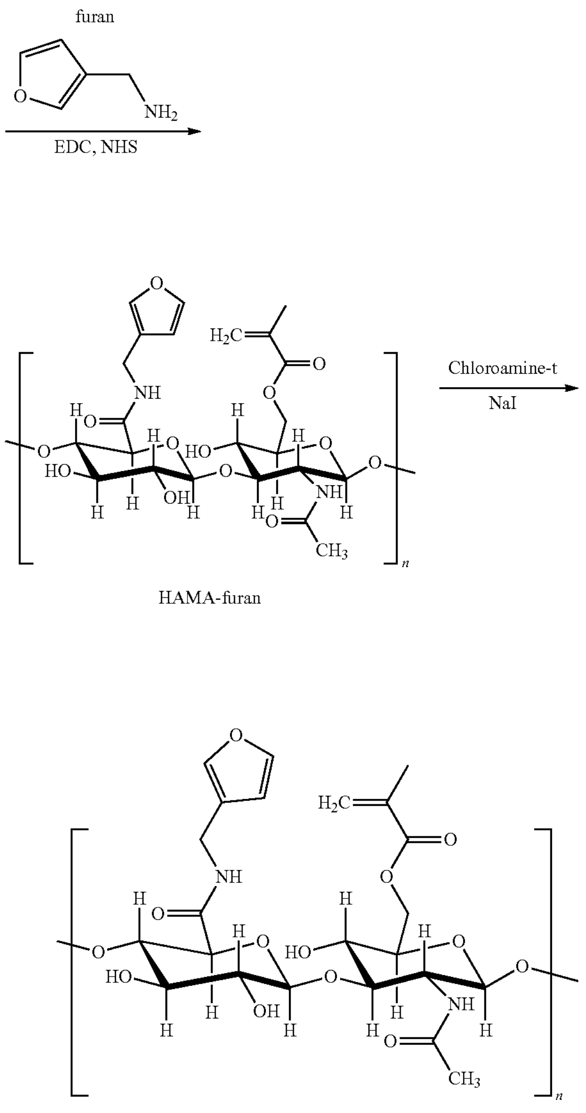

Reaction Scheme 3 shows the preparation process of HAMA-furan-I. After preparing HAMA with improved methacrylate substitution according to the Example 4, 100 mg of HAMA was dissolved in 10 mL PBS (pH 7.4) solution. After adjusting the pH to 5.5 using 1N HCl, 85.5 mg of EDC and 102.7 mg of NHS were added to the solution in the same manner as in the method of preparing HAMA-API of Example 1, followed by stirring for 30 minutes. Thereafter, instead of the API, 119.2 mg of 3-(aminomethyl) furan hydrochloride was added according to the Reaction Scheme 3, followed by stirring at 25° C. for 24 hours. The reaction mixture was dialyzed for 2 days in a pH 5.0 solution, and then dialyzed for 1 day with distilled water. The resulting solution was freeze-dried to obtain a product, and the resulting HAMA-furan solution was prepared, followed by labeling $^{131}I$.

<Preparation Example 4> HAMA-Thiophene-1

[Reaction Scheme 4]

thiophene

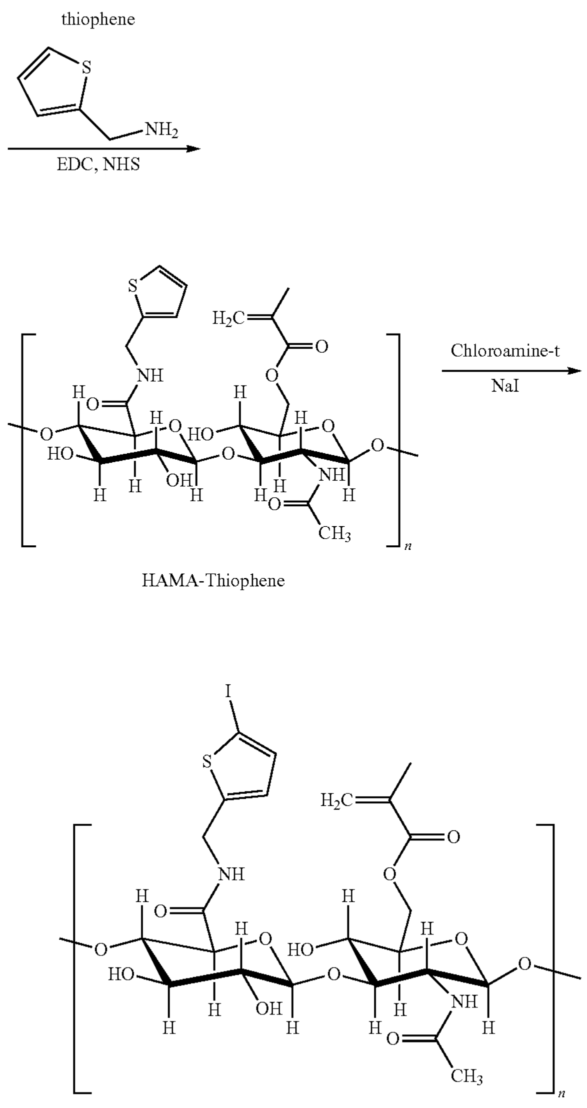

HAMA-Thiophene

HAMA-Thiophene-I

Reaction Scheme 4 shows the preparation process of HAMA-thiophene-I. After preparing HAMA with improved methacrylate substitution according to the Example 4, 100 mg of HAMA was dissolved in 10 mL PBS (pH 7.4) solution. After adjusting the pH to 5.5 using 1N HCl, 85.5 mg of EDC and 102.7 mg of NHS were added to the solution in the same manner as in the method of preparing HAMA-API of the Example 1, followed by stirring for 30 minutes. Thereafter, instead of the API, according to the Reaction Scheme 4, 100.9 mg of 2-thiophene methylamine was added, followed by stirring at 25° C. for 24 hours. The reaction mixture was dialyzed for 2 days in a pH 5.0 solution, and then dialyzed for 1 day with distilled water. The resulting solution was freeze-dried to obtain a product, and the resulting HAMA-thiophene solution was prepared, followed by labeling $^{131}$I.

<Preparation Example 5> HAMA-N-Iodoindole (Derivative 1)

[Reaction Scheme 5]

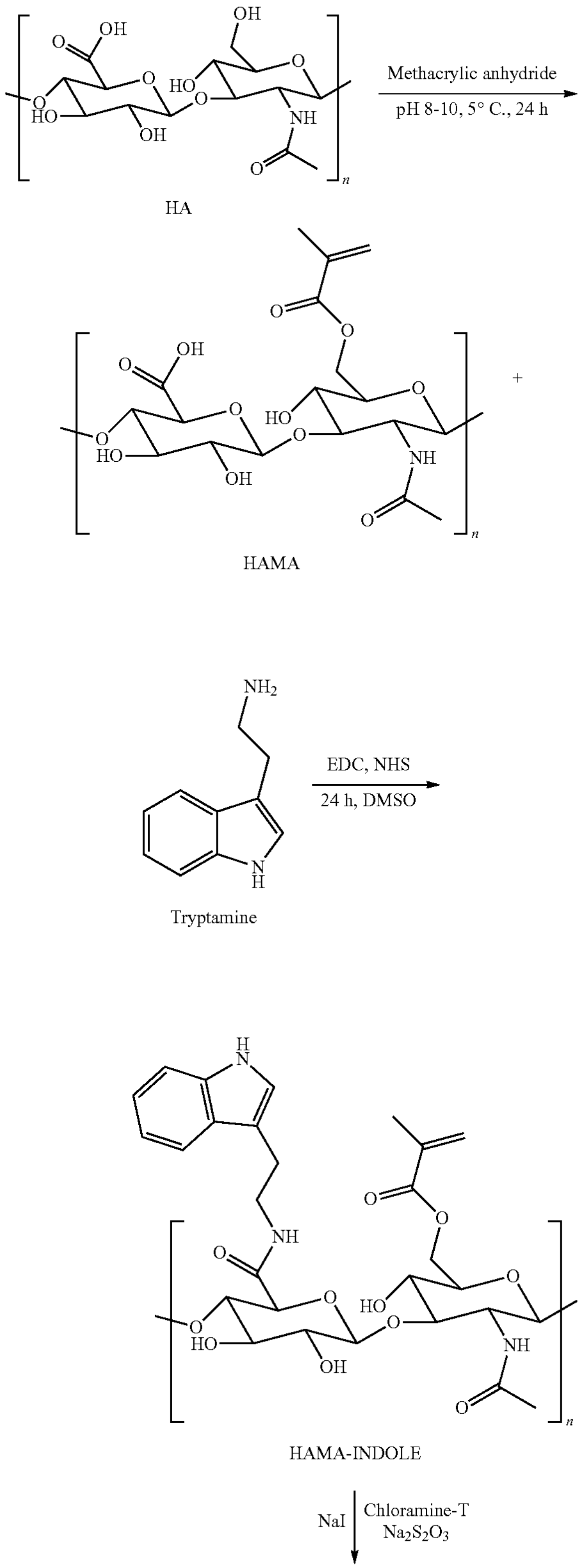

HA

HAMA

Tryptamine

HAMA-INDOLE

-continued

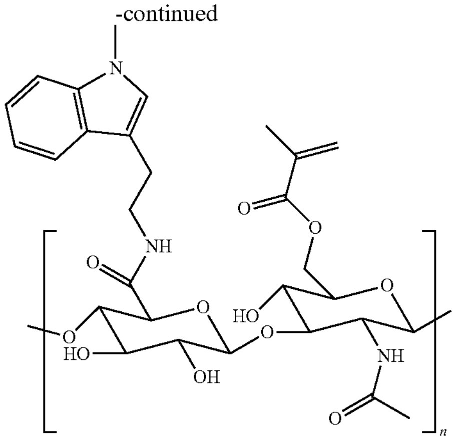

HAMA-N-IODOINDOLE

Reaction Scheme 5 shows the preparation process of HAMA-N-iodoindole. After preparing HAMA with improved methacrylate substitution according to the Example 4, 100 mg of HAMA was dissolved in a 20 mL dimethyl sulfoxide (DMSO) solution. Then, 115.1 mg of EDC and 138.1 mg of NHS were added to the solution in the same manner as in the method of preparing HAMA-API of the Example 1, followed by stirring for 2 hours. Thereafter, instead of the API, 77.5 mg of N-ethyldiisopropylamine was added to the mixture according to the Reaction Scheme 5, and then 96.1 mg of tryptamine was added. The reaction was stirred under nitrogen for 36 hours. The reaction mixture was dialyzed in DMSO solution for 12 hours and then dialyzed with distilled water for 3 days. The resulting solution was freeze-dried to obtain a product, and the resulting HAMA-indole solution was prepared, and then $^{131}I$ was labeled to prepare HAMA-N-iodoindole.

FIG. 20 shows a UV/vis spectrum of HAMA and HAMA-N-indole generated according to a preparation example of the present invention, and FIG. 21 shows $^{1}H$ NMR spectra of a HAMA-N-indole and HAMA-N-iodoindole generated according to a preparation example of the present invention.

While the present invention has been particularly described with reference to specific examples thereof, it is apparent that this specific description is only a preferred example and that the scope of the present invention is not limited thereby to those skilled in the art. That is, the practical scope of the present invention is defined by the appended claims and their equivalents.

The invention claimed is:

1. A photocrosslinkable microhydrogel for radiotherapy, comprising:

a hyaluronic acid-based compound represented by Chemical Formula 1 or a pharmaceutically acceptable salt thereof, wherein the photocrosslinkable hydrogel is injected into a body to stay at an injection site,

[Chemical Formula 1]

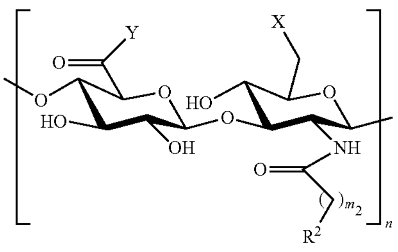

in Chemical Formula 1,

X is photocrosslinkable methacrylate, substituted with a degree of methacrylation (DM) per disaccharide unit of hyaluronic acid is from 100 to 217%, Y is Chemical Formula 2,

[Chemical Formula 2]

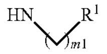

in Chemical Formulae 1 and 2, $R^1$ is selected from the group consisting of imidazole, pyrrole, furan, thiophene, indole and 3,4-dihydroxyphenyl which are capable of labeling one or more radioactive isotopes, $R^2$ is hydrogen, $m_1$ is integer from 1 to 3, $m_2$ is 1, and n is 20 to 4,000, wherein the microhydrogel has an average particle size of 50 to 100 μm.

2. The photocrosslinkable microhydrogel for radiotherapy of claim 1, wherein the radioactive isotope is at least one selected from the group consisting of $^{131}I$, $^{125}I$, $^{124}I$, $^{123}I$, $^{18}F$, $^{19}F$, $^{177}Lu$ and $^{211}At$.

* * * * *